(12) United States Patent
Abhari et al.

(10) Patent No.: US 11,071,593 B2
(45) Date of Patent: Jul. 27, 2021

(54) METHODS AND SYSTEMS FOR PROVIDING VISUOSPATIAL INFORMATION

(71) Applicants: Kamyar Abhari, Toronto (CA); Stewart David McLachlin, Toronto (CA); Kai Michael Hynna, Toronto (CA); Gal Sela, Toronto (CA); Jared Rowland Shoup, Toronto (CA); Michael Peter Bulk, Toronto (CA); Kelly Noel Dyer, Toronto (CA)

(72) Inventors: Kamyar Abhari, Toronto (CA); Stewart David McLachlin, Toronto (CA); Kai Michael Hynna, Toronto (CA); Gal Sela, Toronto (CA); Jared Rowland Shoup, Toronto (CA); Michael Peter Bulk, Toronto (CA); Kelly Noel Dyer, Toronto (CA)

(73) Assignee: Synaptive Medical Inc., Toronto (CA)

(*) Notice: Subject to any disclaimer, the term of this patent is extended or adjusted under 35 U.S.C. 154(b) by 548 days.

(21) Appl. No.: 15/650,253

(22) Filed: Jul. 14, 2017

(65) Prior Publication Data
US 2019/0015162 A1 Jan. 17, 2019

(51) Int. Cl.
*A61B 34/20* (2016.01)
*A61B 34/00* (2016.01)
(Continued)

(52) U.S. Cl.
CPC ............ *A61B 34/20* (2016.02); *A61B 34/25* (2016.02); *A61B 17/3421* (2013.01);
(Continued)

(58) Field of Classification Search
CPC ............ A61B 34/20; A61B 2034/2055; A61B 2034/2065; A61B 34/25;
(Continued)

(56) References Cited

U.S. PATENT DOCUMENTS

| | | |
|---|---|---|
| 2004/0059217 A1 | 3/2004 | Kessman et al. |
| 2007/0225550 A1 | 9/2007 | Gattani et al. |

(Continued)

FOREIGN PATENT DOCUMENTS

WO  2017/015738 A1  2/2017

OTHER PUBLICATIONS

Gard, N. et al. New Tools for Digital Surgical Microscopy [PowerPoint slides]. Retrieved from https://datacloud.hhi.fraunhofer.de/nextcloud/index.php/s/ELtqhsdw7nblVeC.

(Continued)

*Primary Examiner* — Hien N Nguyen
(74) *Attorney, Agent, or Firm* — Ridout & Maybee LLP

(57) ABSTRACT

Methods and systems for providing feedback during a medical procedure. The 3D position and orientation of a tracked tool are determined, relative to a site of the medical procedure, based on tracking information received from a tracking system. The 3D position and orientation are mapped to a common coordinate space, to determine the 3D position and orientation relative to a field-of-view (FOV) of an optical camera that is capturing an optical image of the site. Navigational information associated with the 3D position and orientation is determined. A virtual representation of the navigational information overlaid on the FOV and displayed. The displayed virtual representation is updated when the 3D position and orientation of the tracked tool changes or when the FOV changes, in accordance with the change.

17 Claims, 21 Drawing Sheets

(51) Int. Cl.
- *A61B 17/34* (2006.01)
- *A61B 90/00* (2016.01)
- *A61B 10/04* (2006.01)
- *A61B 34/10* (2016.01)

(52) U.S. Cl.
CPC ... *A61B 2010/045* (2013.01); *A61B 2034/107* (2016.02); *A61B 2034/2051* (2016.02); *A61B 2034/2055* (2016.02); *A61B 2034/2065* (2016.02); *A61B 2034/2068* (2016.02); *A61B 2090/365* (2016.02); *A61B 2090/373* (2016.02); *A61B 2576/026* (2013.01)

(58) Field of Classification Search
CPC ........ A61B 2034/2068; A61B 17/3421; A61B 2090/373; A61B 2034/2051; A61B 2010/045; A61B 2034/107; A61B 2090/365; A61B 2576/026; A61B 90/37
See application file for complete search history.

(56) References Cited

U.S. PATENT DOCUMENTS

| | | |
|---|---|---|
| 2011/0268248 A1 | 11/2011 | Simon et al. |
| 2014/0135746 A1 | 5/2014 | Schoepp |
| 2017/0076501 A1* | 3/2017 | Jagga ............... A61B 34/76 |
| 2017/0245942 A1* | 8/2017 | Penenberg ............ G06T 19/20 |
| 2019/0046276 A1* | 2/2019 | Inglese ............... A61C 9/0046 |

OTHER PUBLICATIONS

Gard, N., et al., "New Tools for Digital Surgical Microscopy", Jun. 22, 2017, CARS, Barcelona.

Search report issued by the Intellectual Property Office of the United Kingdom in relation to corresponding GB application No. GB1811457.9 dated Apr. 30, 2019, 5 pgs.

* cited by examiner

METHODS AND SYSTEMS FOR PROVIDING VISUOSPATIAL INFORMATION

FIELD

The present disclosure relates to methods and systems for providing intraoperative navigational feedback. In particular, the present disclosure relates to providing visuospatial navigational information, using a tracking system and visual overlay.

BACKGROUND

In an example neurosurgical procedure, a surgeon or a robotic surgical system may perform a port-based minimally-invasive procedure involving tumor resection in the brain. A goal of the procedure typically includes minimizing trauma to healthy tissue, such as the intact white and grey matter of the brain. Trauma may occur, for example, due to contact of healthy tissue with the access port, stress to the brain matter, unintentional impact with surgical devices, and/or accidental resection of healthy tissue. In order to reduce trauma, the surgeon should have accurate information, including depth information, about where the surgical tools are relative to the surgical site of interest.

Conventional systems may not provide information about the surgical site in sufficient detail. For example, in conventional procedures, the surgeon is typically provided with a view of the site of interest via a camera or eyepiece of a microscope, endoscope or exoscope. This typically provides only a real-life view of the actual site, without any additional visuospatial information that might help the surgeon. Instead, the surgeon is required to turn to other screens or monitors for additional information, or rely on their own trained visuospatial abilities. This can be taxing to the surgeon and may lead to longer procedures and greater risk of accidental trauma to healthy tissue.

SUMMARY

In some examples, the present disclosure provides a system for providing feedback during a medical procedure. The system includes a tracking system configured to obtain tracking information about three-dimensional (3D) position and orientation of a tracked tool during the medical procedure. The system also includes the tracked tool coupled to tracking markers to enable tracking of the tracked tool by the tracking system. The system also includes a camera for capturing an optical image of a field-of-view (FOV) of a site during the medical procedure. The system also includes a display for displaying the optical image of the FOV. The system also includes a processor coupled to receive input data from the tracking system and the camera, and coupled to transmit output data for display on the display. The processor is configured to determine the 3D position and orientation of the tracked tool, relative to the site, based on the tracking information. The processor is also configured to map the 3D position and orientation to a common coordinate space, to determine the 3D position and orientation relative to the FOV. The processor is also configured to determine navigational information associated with the 3D position and orientation. The processor is also configured to cause the display to display a virtual representation of the navigational information overlaid on the FOV. The processor is also configured to update the displayed virtual representation by: when the 3D position and orientation of the tracked tool changes, updating the displayed virtual representation in accordance with the changed 3D position and orientation; or when the FOV changes, updating the displayed virtual representation to follow the changed FOV.

In some examples, the present disclosure provides a method for providing feedback during a medical procedure. The method includes determining the 3D position and orientation of a tracked tool, relative to a site of the medical procedure, based on tracking information received from a tracking system that is tracking the tracked tool. The method also includes mapping the 3D position and orientation to a common coordinate space, to determine the 3D position and orientation relative to a field-of-view (FOV) of a camera that is capturing an optical image of the site. The method also includes determining navigational information associated with the 3D position and orientation. The method also includes causing a display to display a virtual representation of the navigational information overlaid on the FOV. The method also includes updating the displayed virtual representation by: when the 3D position and orientation of the tracked tool changes, updating the displayed virtual representation in accordance with the changed 3D position and orientation; or when the FOV changes, updating the displayed virtual representation to follow the changed FOV.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DESCRIPTION OF EXAMPLE EMBODIMENTS

Figure 1:
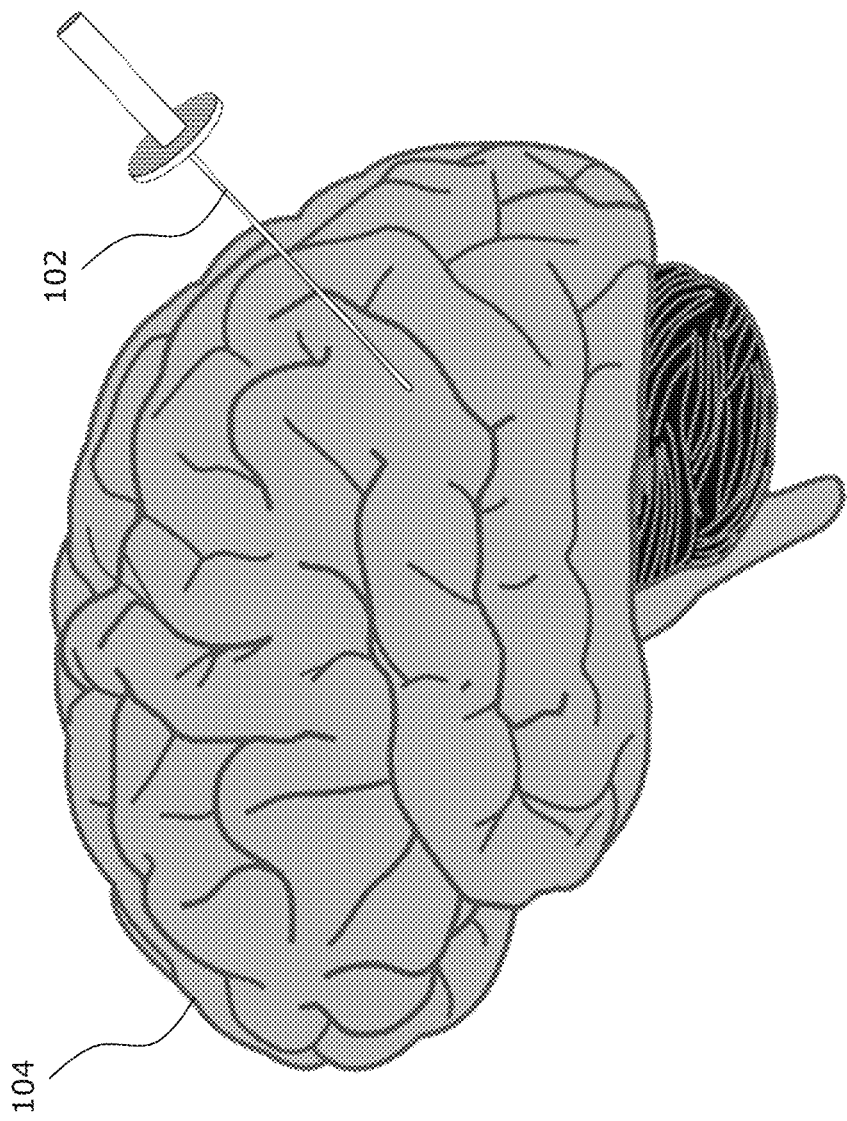
FIG. 1 illustrates the insertion of an access port into a human brain, for providing access to internal brain tissue during an example medical procedure.

The systems and methods described herein may be useful in medical procedures, including surgical procedures. The present disclosure provides examples in the field of neurosurgery, such as for oncological care, treatment of neurodegenerative disease, stroke, and brain trauma. Persons of skill will appreciate the ability to extend these concepts to other conditions or fields of medicine. For example, the present disclosure may also be applicable to the field of spinal surgery or orthopedic surgery, among others. It should be noted that while the present disclosure describes examples in the context of neurosurgery, the present disclosure may be applicable to other procedures that may benefit from providing visuospatial information during the medical procedure.

Visuospatial information that may be provided by methods and systems disclosed herein include navigational information, for example including dimensional information and trajectory information. Dimensional information may include, for example, information about the position and orientation of a tracked tool or target, diameter of a tumour, depth of a cavity, size of a pedicle, angle of approach and/or depth of a target. Trajectory information may include information related to a planned trajectory including, for example, visual indication of the planned trajectory, planned targets and/or updates to the planned trajectory as the view of the site changes.

Further, a surgeon (or other operator) may be able to modify the visuospatial information, for example to mark a point, region or boundary of interest, to change the visual presentation (e.g., contrast, sharpness and/or color) and/or restrict image processing or visuospatial information to a selected area, point, shape and/or property (e.g., to reduce computation time and/or reduce mental load).

Various example apparatuses or processes will be described below. No example embodiment described below limits any claimed embodiment and any claimed embodiments may cover processes or apparatuses that differ from those examples described below. The claimed embodiments are not limited to apparatuses or processes having all of the features of any one apparatus or process described below or to features common to multiple or all of the apparatuses or processes described below. It is possible that an apparatus or process described below is not an embodiment of any claimed embodiment.

Furthermore, numerous specific details are set forth in order to provide a thorough understanding of the disclosure. However, it will be understood by those of ordinary skill in the art that the embodiments described herein may be practiced without these specific details. In other instances, well-known methods, procedures and components have not been described in detail so as not to obscure the embodiments described herein.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" or "example" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

As used herein the phrase "preoperative" refers to an action, process, method, event or step that occurs prior to the start of a medical procedure. Preoperative, as defined herein, is not limited to surgical procedures, and may refer to other types of medical procedures, such as diagnostic and therapeutic procedures. Planning a medical procedure may be considered to be preoperative.

Some embodiments of the present disclosure include imaging devices that are insertable into a subject or patient for imaging internal tissues, and methods of use thereof. Some embodiments of the present disclosure relate to minimally invasive medical procedures that are performed via an access port or retractor tube, whereby surgery, diagnostic imaging, therapy, or other medical procedures (e.g., minimally invasive medical procedures) are performed based on access to internal tissue through the access port or retractor tube.

FIG. 1 illustrates the insertion of an access port into a human brain, for providing access to internal brain tissue during a medical procedure. In FIG. 1, an access port 102 is inserted into a human brain 104, providing access to internal brain tissue. The access port 102 may include such instruments as catheters, surgical probes, or cylindrical ports such as the NICO BrainPath™. Surgical tools and instruments may then be inserted within the lumen of the access port in order to perform surgical, diagnostic or therapeutic procedures, such as resecting tumors, as necessary.

The present disclosure applies equally well to catheters, deep brain stimulation (DBS) needles, a biopsy procedure, and also to biopsies and/or catheters in other medical procedures performed on other parts of the body, as well as to medical procedures that do not use an access port, including non-neural medical procedures, such as spinal procedures.

In the example of a port-based surgery, a straight or linear access port 102 is typically guided down a sulcal path of the brain. Surgical instruments would then be inserted down the access port 102. Optical tracking systems, used in the medical procedure, track the position of a part of the instrument that is within line-of-sight of the optical tracking camera using by the tracking system. Other tracking systems may be used, such as electromagnetic, optical, or mechanical based tracking systems, including tracking systems that use multiple tracking cameras or do not use any tracking camera.

Figure 2:
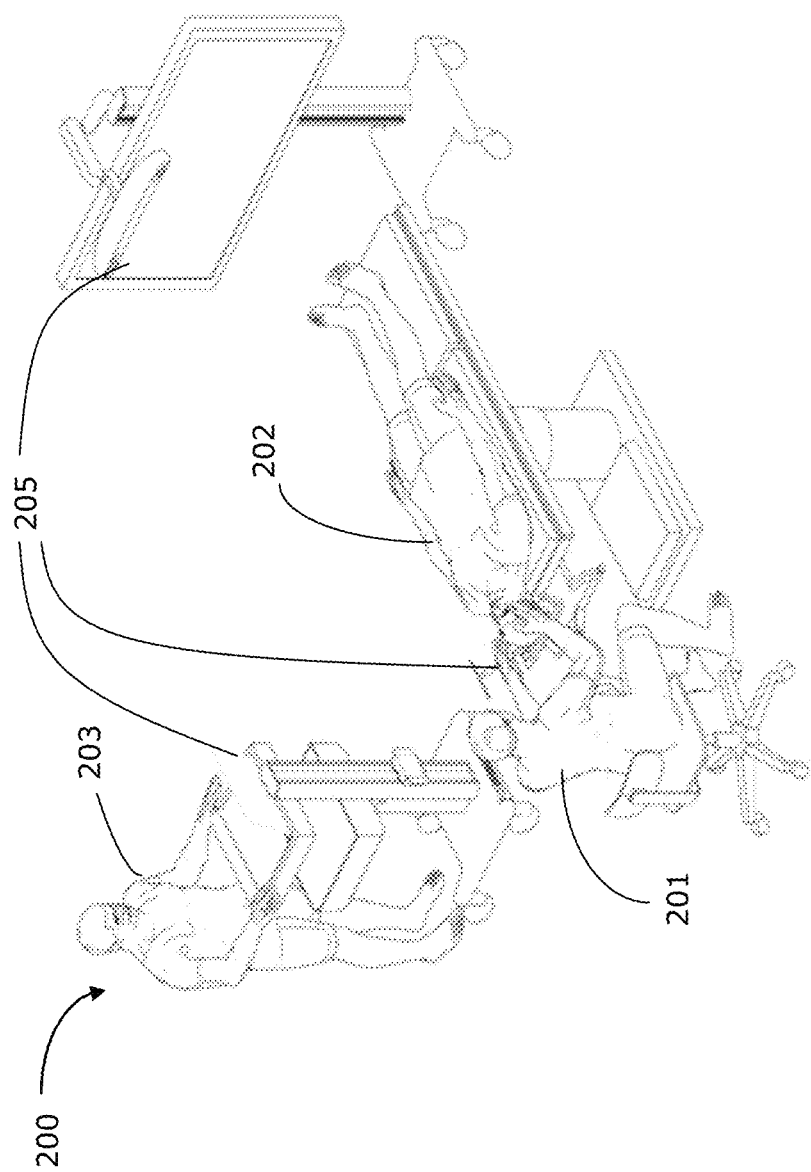
FIG. 2 shows an example navigation system to support image guided surgery.

In FIG. 2, an exemplary navigation system environment 200 is shown, which may be used to support navigated image-guided surgery. As shown in FIG. 2, a surgeon 201 conducts a surgery on a patient 202 in an operating room (OR) environment. A medical navigation system 205 may include an equipment tower, tracking system, displays and tracked instruments to assist the surgeon 201 during the procedure. An operator 203 may also be present to operate, control and provide assistance for the medical navigation system 205.

Figure 3:
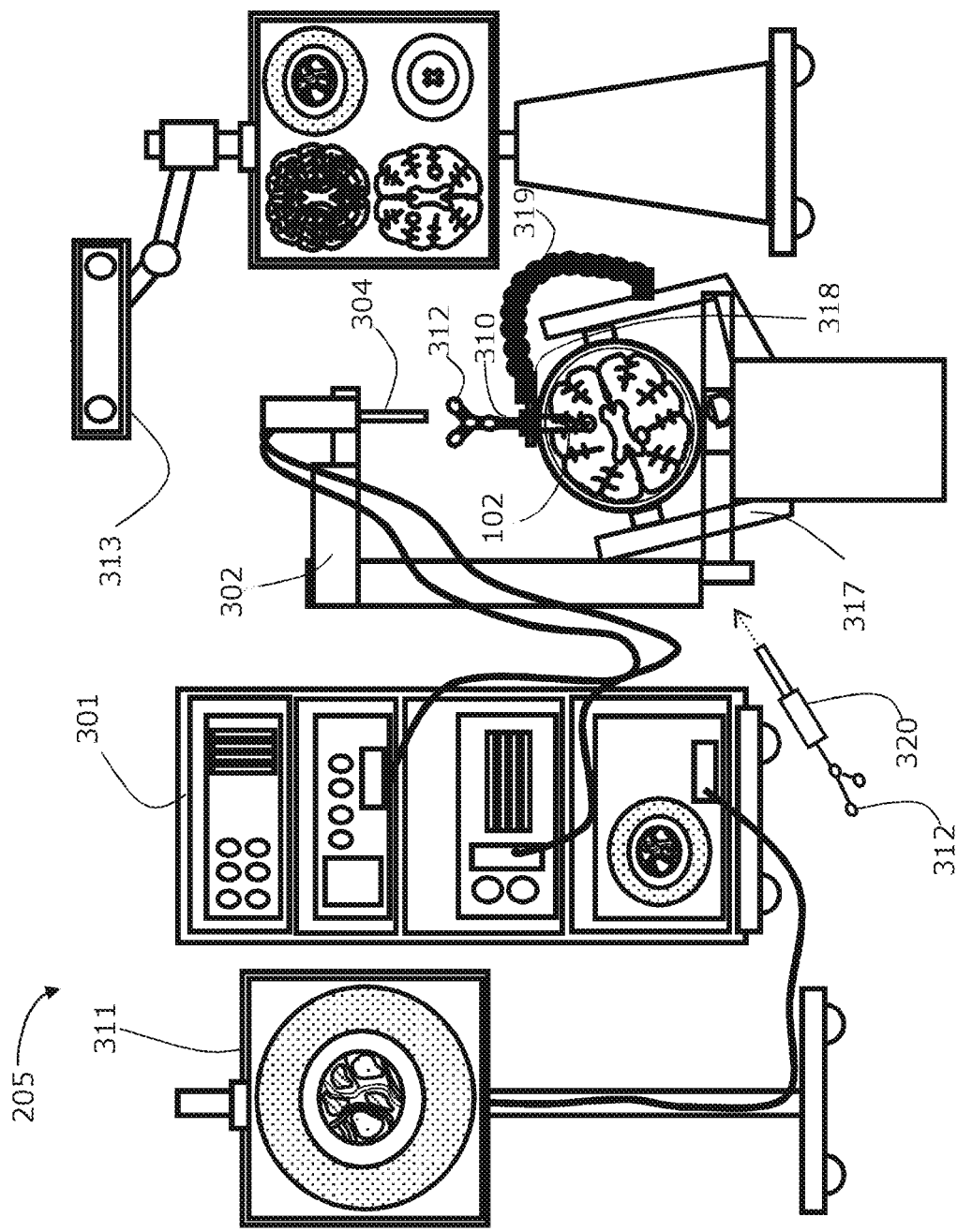
FIG. 3 is a diagram illustrating system components of an example navigation system.

FIG. 3 shows a diagram illustrating components of the example medical navigation system 205. The disclosed methods and systems for providing visuospatial information may be implemented in the context of the medical navigation system 205. The medical navigation system 205 may include one or more displays 311 for displaying still and/or video images (e.g., a live video image of the surgical field and/or 2D or 3D images obtained preoperatively), an equipment tower 301, and a positioning system 302 (e.g., a mechanical arm), which may support an optical scope 304 (which may also be referred to as an external scope). One or more of the displays 311 may include a touch-sensitive display for receiving touch input. The equipment tower 301 may be mounted on a frame (e.g., a rack or cart) and may contain a power supply and a computer or controller that may execute planning software, navigation software and/or other software to manage the positioning system 302 and tracked instruments. In some examples, the equipment tower 301 may be a single tower configuration operating with multiple displays 311, however other configurations may also exist (e.g., multiple towers, single display, etc.). Furthermore, the equipment tower 301 may also be configured with a universal power supply (UPS) to provide for emergency power, in addition to a regular AC adapter power supply.

A portion of the patient's anatomy may be held in place by a holder. For example, in the context of a neurosurgical procedure, the patient's head and brain may be held in place by a head holder 317. An access port 102 and associated introducer 310 may be inserted into the head, to provide access to a surgical site in the head. The optical scope 304 may be attached to the positioning system 302, and may be used to view down the access port 102 at a sufficient magnification to allow for enhanced visibility down the access port 102. The output of the optical scope 304 may be received by one or more computers or controllers to generate a view that may be depicted on a visual display (e.g., one or more displays 311).

In some examples, the navigation system 205 may include a tracked tool 320, which may include or be coupled to one or more markers 312 (also referred to as tracking markers or fiducial markers) to enable tracking by a tracking camera of a tracking system 313 that is part of the navigation system 205. As mentioned above, in various examples the tracking system 313 may have one tracking camera, multiple tracking cameras or no tracking camera. The tracking system 313 may provide, to a processor of the navigation system 205, tracking information indicating the position and orientation of the tracked tool 320, as described further below. An example of a tracked tool 320 may be a pointing tool, which may be used to identify points (e.g., fiducial points or points bordering a craniotomy opening, as discussed below) on a patient. For example, an operator, typically a nurse or the surgeon 201, may use the pointing tool to identify the location of points on the patient 202, in order to register the location of selected points on the patient 202 in the navigation system 205. A tracked tool 320 may also be a suction tool. In addition to providing suction, the distal end of the suction tool may be used for pointing, similarly to the distal end of a pointing tool. It should be noted that a guided robotic system may be used as a proxy for human interaction. Guidance to the robotic system may be provided by any combination of input sources such as image analysis, tracking of objects in the operating room using markers placed on various objects of interest, or any other suitable robotic system guidance techniques.

One or more markers 312 may also be coupled to the introducer 310 to enable tracking by the tracking system 313, and the tracking system 313 may provide, to a processor of the navigation system 205, tracking information indicating the position and orientation of the introducer 310. In some examples, the markers 312 may be alternatively or additionally attached to the access port 102. Other tools (not shown) may be provided with markers 312 to enable tracking by the tracking system 313.

In some examples, the tracking camera used by the tracking system 313 may be a 3D infrared optical tracking stereo camera similar to one made by Northern Digital Imaging (NDI). In some examples, the tracking system 313 may be an electromagnetic system (not shown). An electromagnetic tracking system may include a field transmitter and the tracking markers 312 may include receiver coils coupled to the tool(s) 320 to be tracked. The known profile of the electromagnetic field and the known position of receiver coil(s) relative to each other may be used to infer the location of the tracked tool(s) 320 using the induced signals and their phases in each of the receiver coils. Operation and examples of this technology is further explained in Chapter 2 of "Image-Guided Interventions Technology and Application," Peters, T.; Cleary, K., 2008, ISBN: 978-0-387-72856-7, incorporated herein by reference.

Tracking information of the positioning system 302 and/or access port 102 may be determined by the tracking system 313 by detection of the markers 312 placed on or otherwise in fixed relation (e.g., in rigid connection) to any of the positioning system 302, the access port 102, the introducer 310, the tracked tool 320 and/or other tools.

The marker(s) 312 may be active or passive markers. Active markers may include infrared emitters for use with an optical tracking system, for example. Passive markers may include reflective spheres for use with an optical tracking system, or pick-up coils for use with an electromagnetic tracking system, for example.

The markers 312 may all be the same type or may include a combination of two or more different types. Possible types of markers that could be used may include reflective markers, radiofrequency (RF) markers, electromagnetic (EM) markers, pulsed or un-pulsed light-emitting diode (LED) markers, glass markers, reflective adhesives, or reflective unique structures or patterns, among others. RF and EM markers may have specific signatures for the specific tools they may be attached to. Reflective adhesives, structures and patterns, glass markers, and LED markers may be detectable using optical detectors, while RF and EM markers may be detectable using antennas. Different marker types may be selected to suit different operating conditions. For example, using EM and RF markers may enable tracking of tools without requiring a line-of-sight from the tracking camera to the markers 312, and using an optical tracking system 313 may avoid additional noise from electrical emission and detection systems.

In some examples, the markers 312 may include printed or 3D designs that may be used for detection by an auxiliary camera, such as a wide-field camera (not shown) and/or the optical scope 304. Printed markers may also be used as a calibration pattern, for example to provide distance information (e.g., 3D distance information) to an optical detector. Printed identification markers may include designs such as concentric circles with different ring spacing and/or different types of bar codes, among other designs. In some examples, in addition to or in place of using markers 312, the contours of known objects (e.g., the side of the access port 102) could be captured by and identified using optical imaging devices and the tracking system 313.

The markers 312 may be captured by the tracking camera (which may be a stereo camera) to give identifiable points for tracking the tool(s) 320. A tracked tool 320 may be defined by a grouping of markers 312, which may define a rigid body to the tracking system 313. This may in turn be used to determine the position and/or orientation in 3D of a tracked tool 320 in a virtual space. The position and orientation of the tracked tool 320 in 3D may be tracked in six degrees of freedom (e.g., x, y, z coordinates and pitch, yaw, roll rotations), in five degrees of freedom (e.g., x, y, z, coordinate and two degrees of free rotation), but typically tracked in at least three degrees of freedom (e.g., tracking the position of the tip of a tool in at least x, y, z coordinates). In typical use with the navigation system 205, at least three markers 312 are provided on a tracked tool 320 to define the tool 320 in virtual space, however it may be advantageous for four or more markers 312 to be used.

Camera images capturing the markers 312 may be logged and tracked, by, for example, a closed circuit television (CCTV) camera. The markers 312 may be selected to enable or assist in segmentation in the captured images. For example, infrared (IR)-reflecting markers and an IR light source from the direction of the tracking camera may be used. An example of such an apparatus may be tracking devices such as the Polaris® system available from Northern Digital Inc. In some examples, the spatial position of the tracked tool 320 and/or the actual and desired position of the positioning system 302 may be determined by optical detection using the tracking camera. The optical detection may be done using an optical camera, rendering the markers 312 optically visible.

Different tracked tools and/or tracked targets may be provided with respective sets of markers 312 in different configurations. Differentiation of the different tools and/or targets and their corresponding virtual volumes may be possible based on the specification configuration and/or orientation of the different sets of markers 312 relative to one another, enabling each such tool and/or target to have a distinct individual identity within the navigation system 205. The individual identifiers may provide information to the navigation system 205, such as information relating to the size and/or shape of the tool 320 within the system 205. The identifier may also provide additional information such as the tool's central point or the tool's central axis, among other information. The markers 312 may be tracked relative to a reference point or reference object in the operating room, such as one or more reference points on the patient 202.

The display 311 may provide output of the computed data of the navigation system 205. In some examples, the output provided by the display 311 may include axial, sagittal and coronal views of patient anatomy as part of a multi-view output. In some examples, the one or more displays 311 may include an output device, such as a wearable display device, to provide an augmented reality (AR) display of the site of interest.

A guide clamp 318 (or more generally a guide) for holding the access port 102 may be provided. The guide clamp 318 may allow the access port 102 to be held at a fixed position and orientation while freeing up the surgeon's hands. An articulated arm 319 may be provided to hold the guide clamp 318. The articulated arm 319 may have up to six degrees of freedom to position the guide clamp 318. The articulated arm 319 may be lockable to fix its position and orientation, once a desired position is achieved. The articulated arm 319 may be attached or attachable to a point based on the patient head holder 317, or another suitable point (e.g., on another patient support, such as on the surgical bed), to ensure that when locked in place, the guide clamp 318 does not move relative to the patient's head.

In a surgical operating room (or theatre), setup of a navigation system may be relatively complicated; there may be many pieces of equipment associated with the medical procedure, as well as elements of the navigation system 205. Further, setup time typically increases as more equipment is added. The surgeon 201 may be required to process many sets of information from different equipment during the medical procedure. Information may be primarily of a visual nature, and the surgeon 201 may easily be overwhelmed by the amount of information to be processed. To assist in addressing this, the navigation system 205 may include two additional wide-field cameras to enable information to be overlaid on a real-time view of the site of interest. One wide-field camera may be mounted on the optical scope 304, and a second wide-field camera may be mounted on the tracking camera. Video overlay information can then be added to displayed images, such as images displayed on one or more of the displays 300. The overlaid information may provide visuospatial information, such as indicating the physical space where accuracy of the 3D tracking system is greater, the available range of motion of the positioning system 302 and/or the optical scope 304, and/or other navigational information, as discussed further below.

Although described in the present disclosure in the context of port-based neurosurgery (e.g., for removal of brain tumors and/or for treatment of intracranial hemorrhages (ICH)), the navigation system 205 may also be suitable for one or more of: brain biopsy, functional/deep-brain stimulation, catheter/shunt placement (in the brain or elsewhere), open craniotomies, and/or endonasal/skull-based/ear-nose-throat (ENT) procedures, as well as procedures other than neurosurgical procedures. The same navigation system 205 may be used for carrying out any or all of these procedures, with or without modification as appropriate.

For example, the same navigation system 205 may be used to carry out a diagnostic procedure, such as brain biopsy. A brain biopsy may involve the insertion of a thin needle into a patient's brain for purposes of removing a sample of brain tissue. The brain tissue may be subsequently assessed by a pathologist to determine if it is cancerous, for example. Brain biopsy procedures may be conducted with or without a stereotactic frame. Both types of procedures may be performed using image-guidance. Frameless biopsies, in particular, may be conducted using the navigation system 205.

In some examples, the tracking system 313 may be any suitable tracking system. In some examples, the tracking system 313 may be any suitable tracking system which may or may not use camera-based tracking techniques. For example, a tracking system 313 that does not use the tracking camera, such as a radiofrequency tracking system, may be used with the navigation system 205.

Figure 4:
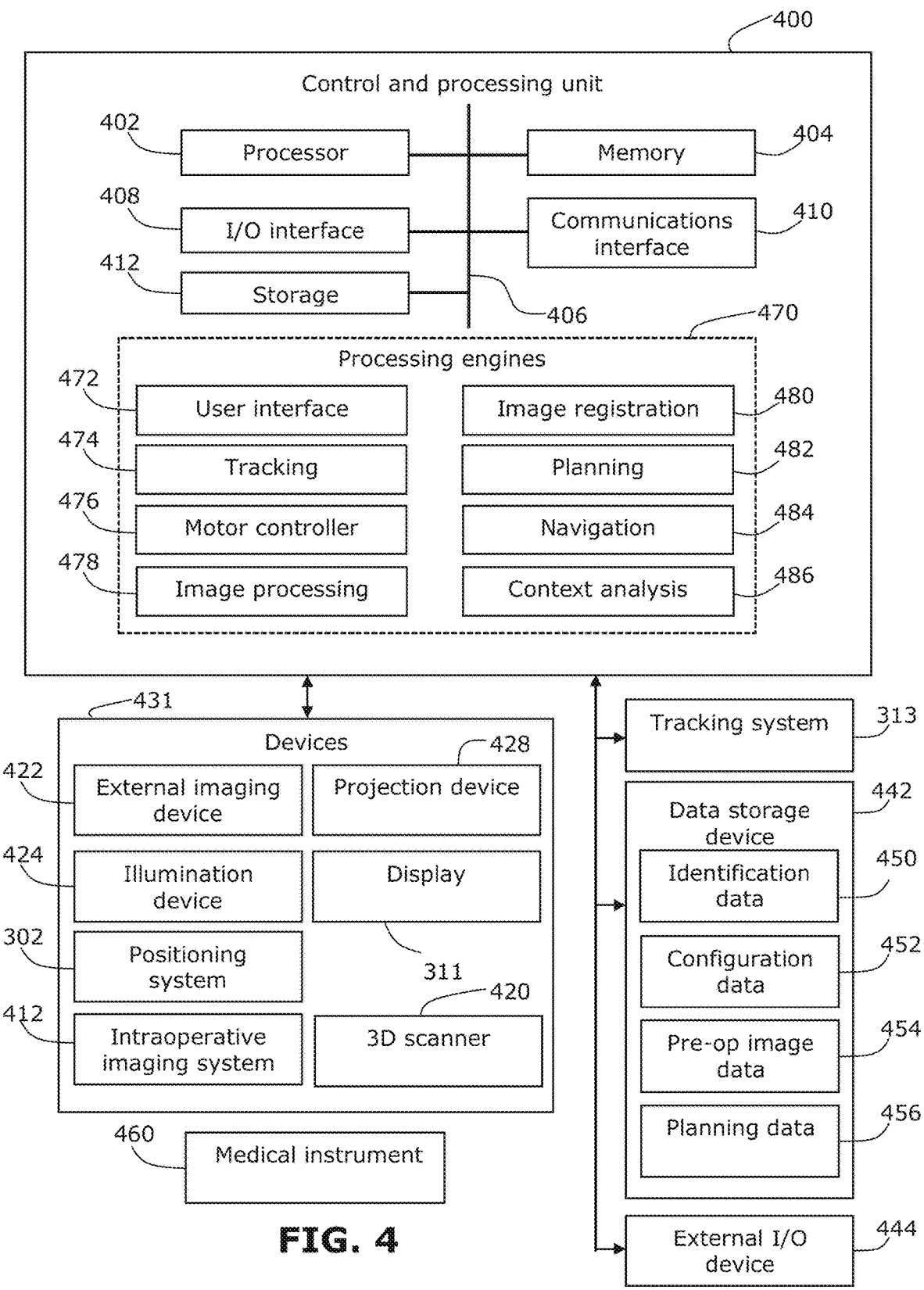
FIG. 4 is a block diagram illustrating an example control and processing system that may be used in the navigation system of FIG. 2.

In FIG. 4, a block diagram is shown illustrating a control and processing system 400 that may be used in the medical navigation system 205 shown in FIG. 3 (e.g., as part of the equipment tower). As shown in FIG. 4, in an example, the control and processing system 400 may include one or more processors 402, a memory 404, a system bus 406, one or more input/output interfaces 408, a communications interface 410, and a storage device 412. The control and processing system 400 may be interfaced with other external devices, such as a tracking system 313, data storage 442, and external user input and output devices 444, which may include, for example, one or more of a display, keyboard, mouse, sensors attached to medical equipment, foot pedal, and microphone and speaker. The data storage 442 may be any suitable data storage device, such as a local or remote computing device (e.g. a computer, hard drive, digital media device, or server) having a database stored thereon. In the example shown in FIG. 4, the data storage device 442 includes identification data 450 for identifying one or more medical instruments 460 (e.g., a tracked tool, such as a pointing tool 320) and configuration data 452 that associates customized configuration parameters with one or more of the medical instrument(s) 460. The data storage device 442 may also include preoperative image data 454 and/or medical procedure planning data 456. Although the data storage device 442 is shown as a single device in FIG. 4, it will be understood that in other embodiments, the data storage device 442 may be provided as multiple storage devices.

The medical instruments 460 may be identifiable by the control and processing unit 400. The medical instruments 460 may be connected to and controlled by the control and processing unit 400, or the medical instruments 460 may be operated or otherwise employed independent of the control and processing unit 400. The tracking system 313 may be employed to track one or more medical instruments 460 and spatially register the one or more tracked medical instruments to an intraoperative reference frame. For example, the medical instruments 460 may include tracking markers 312 as described above with reference to FIG. 3.

The control and processing unit 400 may also interface with a number of configurable devices, and may intraoperatively reconfigure one or more of such devices based on configuration parameters obtained from the configuration data 452. Examples of devices 431, as shown in FIG. 4, include one or more external imaging devices 422, one or more illumination devices 424, a positioning system 302 (e.g., a robotic arm), an imaging device 412, one or more projection devices 428, one or more displays 311, and a scanner 420, which in an example may be a 3D scanner.

Exemplary aspects of the disclosure can be implemented via the processor(s) 402 and/or memory 404. For example, the functionalities described herein can be partially implemented via hardware logic in the processor 402 and partially using the instructions stored in the memory 404, as one or more processing modules or engines 470. Example processing modules include, but are not limited to, a user interface engine 472, a tracking module 474, a motor controller 476, an image processing engine 478, an image registration engine 480, a procedure planning engine 482, a navigation engine 484, and a context analysis module 486. While the example processing modules are shown separately in FIG. 4, in some examples the processing modules 470 may be stored in the memory 404 and the processing modules 470 may be collectively referred to as processing modules 470. In some examples, two or more modules 470 may be used together to perform a function. Although depicted as separate modules 470, the modules 470 may be embodied as a unified set of computer-readable instructions (e.g., stored in the memory 404) rather than distinct sets of instructions.

It is to be understood that the system is not intended to be limited to the components shown in FIG. 4. One or more components of the control and processing system 400 may be provided as an external component or device. In one example, the navigation module 484 may be provided as an external navigation system that is integrated with the control and processing system 400.

Some embodiments may be implemented using the processor 402 without additional instructions stored in memory 404. Some embodiments may be implemented using the instructions stored in memory 404 for execution by one or more general purpose microprocessors. Thus, the disclosure is not limited to a specific configuration of hardware and/or software.

In some examples, the navigation system 205, which may include the control and processing unit 400, may provide tools to the surgeon that may help to improve the performance of the medical procedure and/or post-operative outcomes. In addition to removal of brain tumours and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, examples of the present disclosure may be applied to any suitable medical procedure.

When performing a medical procedure using a medical navigation system 205, the medical navigation system 205 typically acquires and maintains a reference of the location of the tools in use as well as the patient in 3D space. In other words, during a navigated medical procedure, there typically is a tracked reference frame that is fixed relative to the patient. For example, during the registration phase of a navigated neurosurgery, a transformation is calculated that maps the frame of reference of preoperative magnetic resonance (MR) or computed tomography (CT) imagery to the physical space of the surgery, specifically the patient's head. This may be accomplished by the navigation system 205 tracking locations of fiducial markers fixed to the patient's head, relative to the static patient reference frame. The patient reference frame is typically rigidly attached to the head fixation device, such as a Mayfield clamp. Registration is typically performed before the sterile field has been established.

Figure 5:
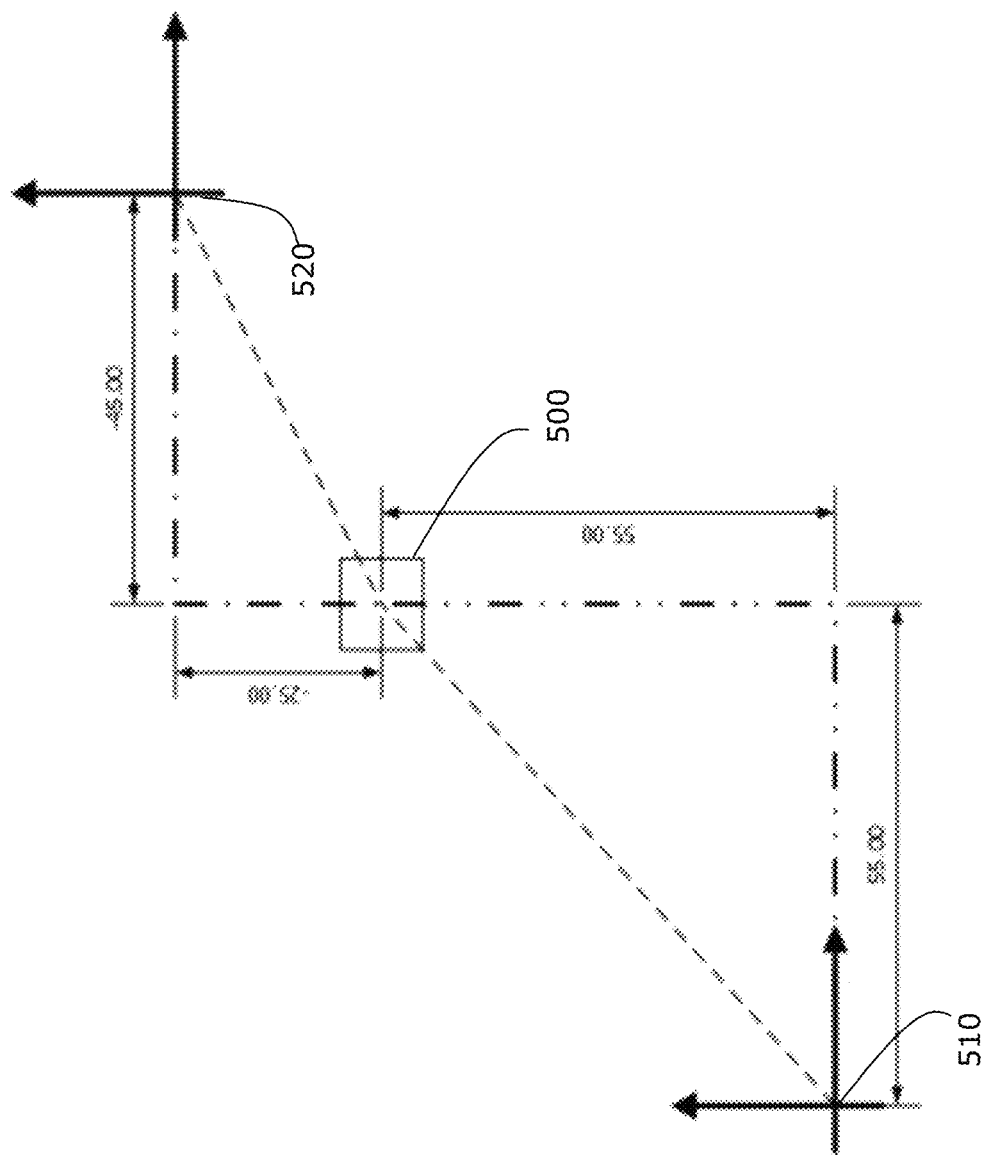
FIG. 5 is a diagram illustrating co-registration of two coordinate spaces.

FIG. 5 illustrates a simplified example of how two coordinate spaces may be co-registered by performing a transformation mapping, based on a common reference coordinate. In the example shown, a common reference coordinate 500 has a defined position and orientation in first and second coordinate spaces 510, 520. In the context of a medical procedure, the common reference coordinate 500 may be a fiducial marker or anatomical reference. Although FIG. 5 illustrates co-registration of 2D coordinate spaces, for simplicity, co-registration may be performed for 3D coordinate spaces, including a depth dimension.

The position and orientation of the common reference coordinate 500 is used to correlate the position of any point in the first coordinate space 510 to the second coordinate space 520, and vice versa. The correlation is determined by equating the locations of the common reference coordinate 500 in both spaces 510, 520 and solving for a transformation variable for each degree of freedom defined in the two coordinate spaces 510, 520. These transformation variables may then be used to transform a coordinate element of a position in the first coordinate space 510 to an equivalent coordinate element of a position in the second coordinate space 520, and vice versa.

In FIG. 5, the common reference coordinate 500 has a coordinate position (x1, y1) determined in the first coordinate space 510 and a coordinate position (x2, y2) in the second coordinate space 520. In the example shown, (x1, y1)=(55, 55) and (x2, y2)=(−45, −25).

Utilizing transformation equations, any point in the first coordinate space 510 may be related to the second coordinate space 520 via translation variables (xT, yT), as shown below:

$$x1=x2+xT$$

$$y1=y2+yT$$

Using the coordinate positions of the common reference coordinate 500, the transformation variables may be solved as follows:

$$55=-45+yT$$

$$100=yT$$

$$55=-25+xT$$

$$80=xT$$

The transformation variables may then be used to transform any coordinate point in the first coordinate space 510 to the second coordinate space 520, and vice versa, thereby co-registering the coordinate spaces 510, 520. For transformation between 3D coordinate spaces, similar calculations may be performed for position (x, y, z-coordinates) as well as for orientation (pitch, yaw, roll). In general, a transformation mapping may be performed to register two or more coordinate spaces with each other. Where there are more than two coordinate spaces to be co-registered, the transformation mapping may include multiple mapping steps.

In some examples, using a handheld 3D scanner 420, a full or nearly full array scan of a surface of interest can be achieved intraoperatively. This may provide an order of magnitude greater point information than the surface tracking methods used in conventional approaches. The intraoperative image data obtained by the 3D scanner 420 may be provided as a 3D point cloud, in an intraoperative image coordinate space. This point cloud may be mapped to a surface in preoperative image data (e.g., MR or CT volumetric scan data), using a reference marker that is imageable by both preoperative and intraoperative imaging systems. The tracking system 313 may have no reference to the 3D point cloud data. Therefore, a transformation mapping between the tracking coordinate space and the intraoperative image coordinate space may be used so that tracking data can also be registered to the preoperative and intraoperative image data.

In the context of the navigation system 205, the co-registration process described above may be used to co-register a tracking coordinate space (which defines the coordinates used by tracking information produced by the tracking system); a medical image coordinate space (which defines the coordinates used by medical image data produced by pre-operative or intra-operative imaging, such as MRI or CT); and a camera coordinate space (which defines the coordinates used by captured image data produced by an optical camera). For example, a first transformation mapping may be performed to map two of the three coordinate spaces to each other (e.g., mapping tracking coordinate space and medical image coordinate space to each other), then a second mapping may be performed to map the remaining coordinate space to the first mapping (e.g., mapping the camera coordinate space to the previous mapping). Thus, a common coordinate space is obtained in which a first object having coordinates defined in one space can be readily related to a second object having coordinates defined in another space. In some examples, the common coordinate space may also be referred to as a unified coordinate space.

Methods and systems disclosed herein may provide spatially-accurate and spatially-persistent visual information on a display. This may be enabled by the combined use of the tracked medical instrument (and other targets), tracked camera and image processing by the navigation system. Tracking of targets enables spatial accuracy, while tracking of the camera enables spatial persistence. In the present disclosure, the term spatial accuracy may be used to refer to the ability to accurately and precisely determine the position (e.g., x,y,z-coordinates) and orientation (e.g., $\varphi,\theta,\psi$ angles) of a tracked tool in a certain coordinate space. The position of an object may generally refer to the coordinate position of a reference point on the object, such as a distal tip of a pointing tool. The orientation of an object may generally refer to the angular orientation of a central axis on the object, such as the central longitudinal axis of a pointing tool. The term spatial persistence may be used to refer to the ability to store and maintain spatial accuracy of a tracked tool in a certain coordinate space even as the field of view of the camera changes. For example, where a visual indication of a tracked tool is superimposed on an image captured by the camera, when the field-of-view (FOV) changes (e.g., camera changes position), the visual indication is updated to reflect the position and orientation of the tracked tool in the new FOV, while maintaining spatial accuracy. That is, information and feedback about the tracked tool is not lost when the FOV changes.

Figure 6A:
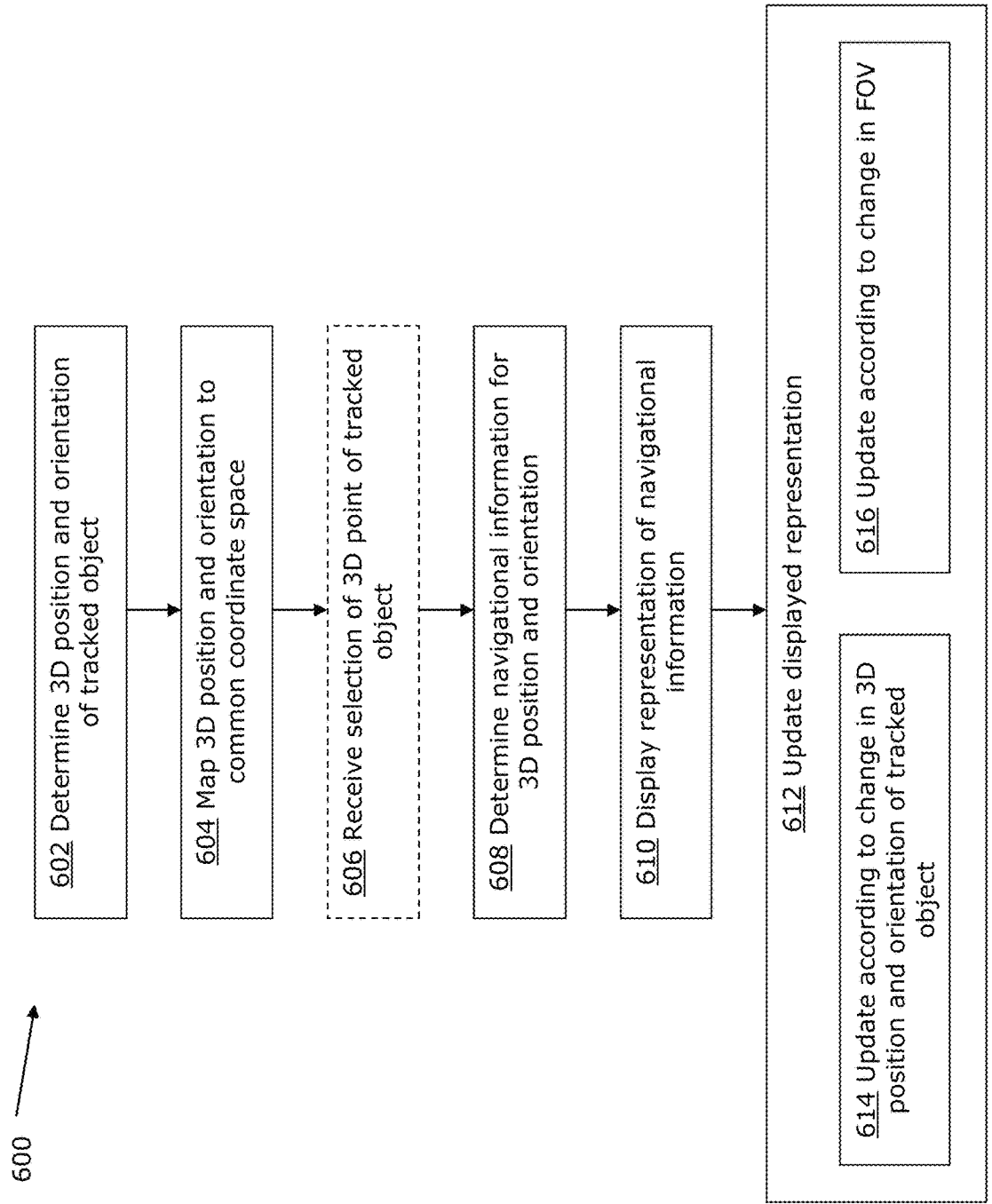
FIG. 6A is a flowchart illustrating an example method for providing intraoperative visuospatial information.
Figure 7A:
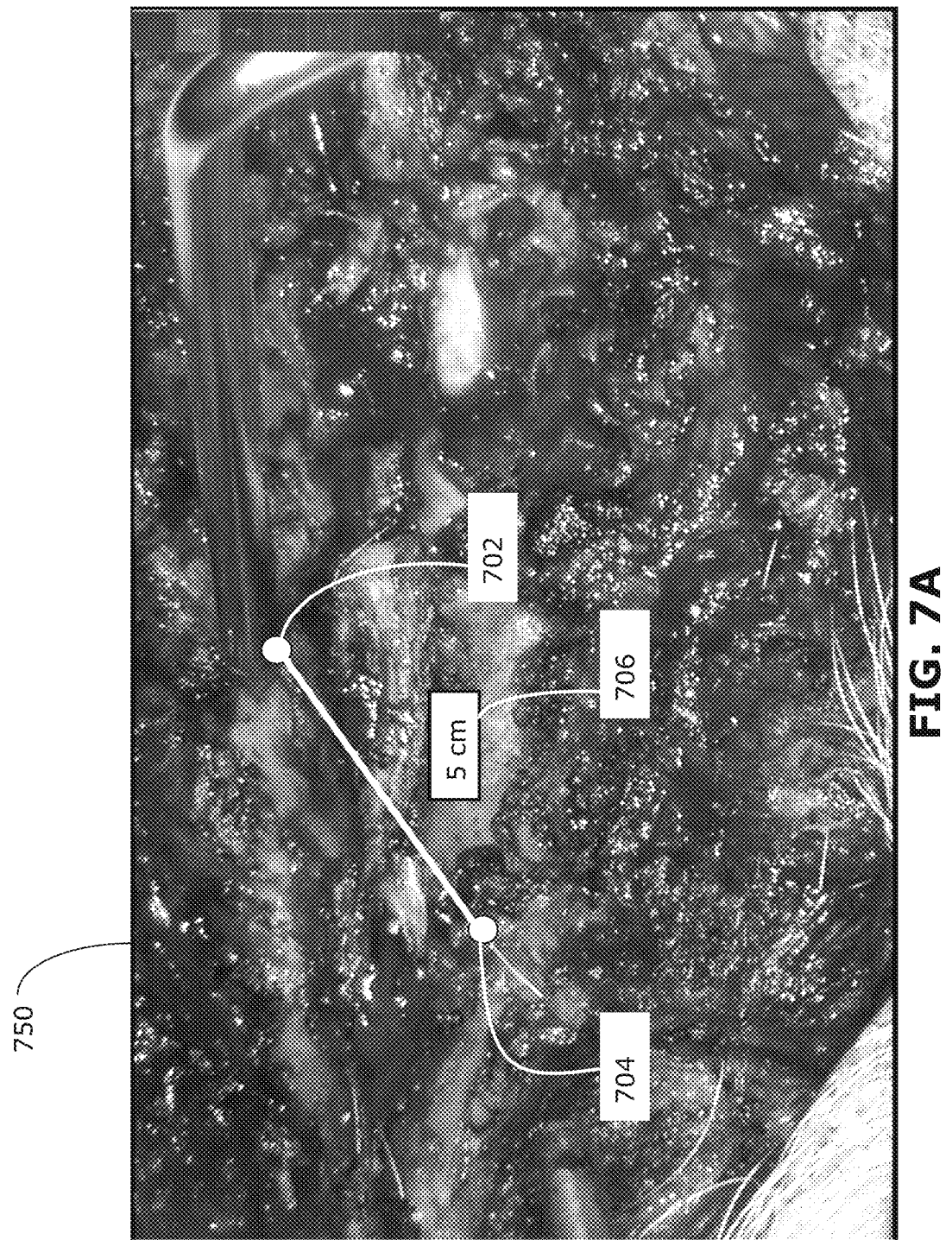
FIG. 7A shows an example display of a captured image including visual representation of selected 3D points.

FIG. 6A is a flowchart illustrating an example method 600 for providing feedback during a medical procedure, for example using the navigation system 205 described above. The example method 600 may be implemented during a neurosurgical procedure, for example as shown in FIG. 7A. An example implementation of the method 600 will be described below with reference to FIG. 7A. Other example implementations will also be provided further below.

The method 600 may take place in the context of an image-guided medical procedure. A tracking system 313 (which may be part of the navigation system 205) may track a tracked tool, such as a pointing tool having tracking markers 312, and provide tracking information about the 3D position and orientation of the tracked tool during the procedure. An optical camera (such as the tracking camera which may be part of the navigation system 205) may capture an image of the medical procedure. The camera may typically be positioned and oriented to capture a FOV of the site, and may be moved to a different position and orientation and/or adjusted to have a different zoom, in order to capture a different FOV of the site. A display (such as the display 311 of the navigation system 205) may be used to display the captured image, and also to display other navigation information. The method 600 may be carried out by a processor (e.g., in a control and processing system of the navigation system 205) coupled to receive the tracking information from the tracking system 313, to receive image data from the camera and to output data to be displayed on the display.

The position and orientation of the camera may be tracked, for example by placing tracking markers on the camera and using the tracking system. The tracked position of the camera may be determined relative to the tracking coordinate space and mapped to the common coordinate space. In some examples, the position and orientation of the camera may be determined based on the position of a positioning system (e.g., a robotic arm) where the camera is supported in a known position and orientation relative to the positioning system. For example, the positioning system may be tracked using tracking markers placed on the positioning system. In another example, the positioning system may include position sensors which provide information about the position of the positioning system. Regardless of how the position and orientation of the camera is determined, this information enables the image captured by the camera to be mapped to a common coordinate space. In some examples, calibration of the camera may be performed (e.g., as part of the method 600 or prior to the method 600) to map pixel positions of the captured image to 3D coordinates in the real world. Any suitable method may be used for such calibration.

At 602, the 3D position and orientation of the tracked tool is determined. The tracking information from the tracking system is used to determine the position and orientation of the tracked tool relative to the site of the procedure. The 3D position and orientation of the tracked tool may be repeatedly determined in real-time by the tracking system, so that the tracking information provides real-time information about the tracked tool. In the example shown in FIG. 7A, the tracked tool is a pointing tool having tracking markers (e.g., reflective spheres) detectable by a tracking system. In particular, the tracked point may be the distal tip of the pointing tool and the orientation of the pointing tool may be defined by the orientation of the central longitudinal axis of the pointing tool. Any object detectable by the tracking system may be the tracked tool, including, for example, any other medical tool such as a suction tool. The tracked point and orientation of the tracked tool may be defined depending on the tracked tool. For example, where the tracked tool has a bent shape (e.g., an L-shaped object), the orientation of the tracked tool may be defined by the longitudinal axis of the most distal portion of the object.

At 604, the 3D position and orientation of the tracked tool is mapped to the common coordinate space. This may be performed by transforming the tracking information from the coordinate space of the tracking system to the common coordinate space. As described previously reference points on the surgical site may also be mapped to the common coordinate space. As well, the FOV of the camera is also mapped to the common coordinate space (e.g., by tracking the position and orientation of the optical camera, using the tracking system and mapping the resulting information to the common coordinate space). Hence, the real-time 3D position and orientation of the tracked tool can be related to the surgical site and also to the FOV of the camera.

At 606, optionally, a selection of a 3D point is received. The 3D point may be selected by positioning the tracked tool at a desired location and activating an input mechanism to select the point. For example, the distal tip of the pointing tool may be placed at a desired location and an input mechanism (e.g., a button on the pointing tool or a foot pedal coupled to the navigation system) may be activated to indicate selection of the position of the distal tip as the selected 3D point.

Figure 6B:
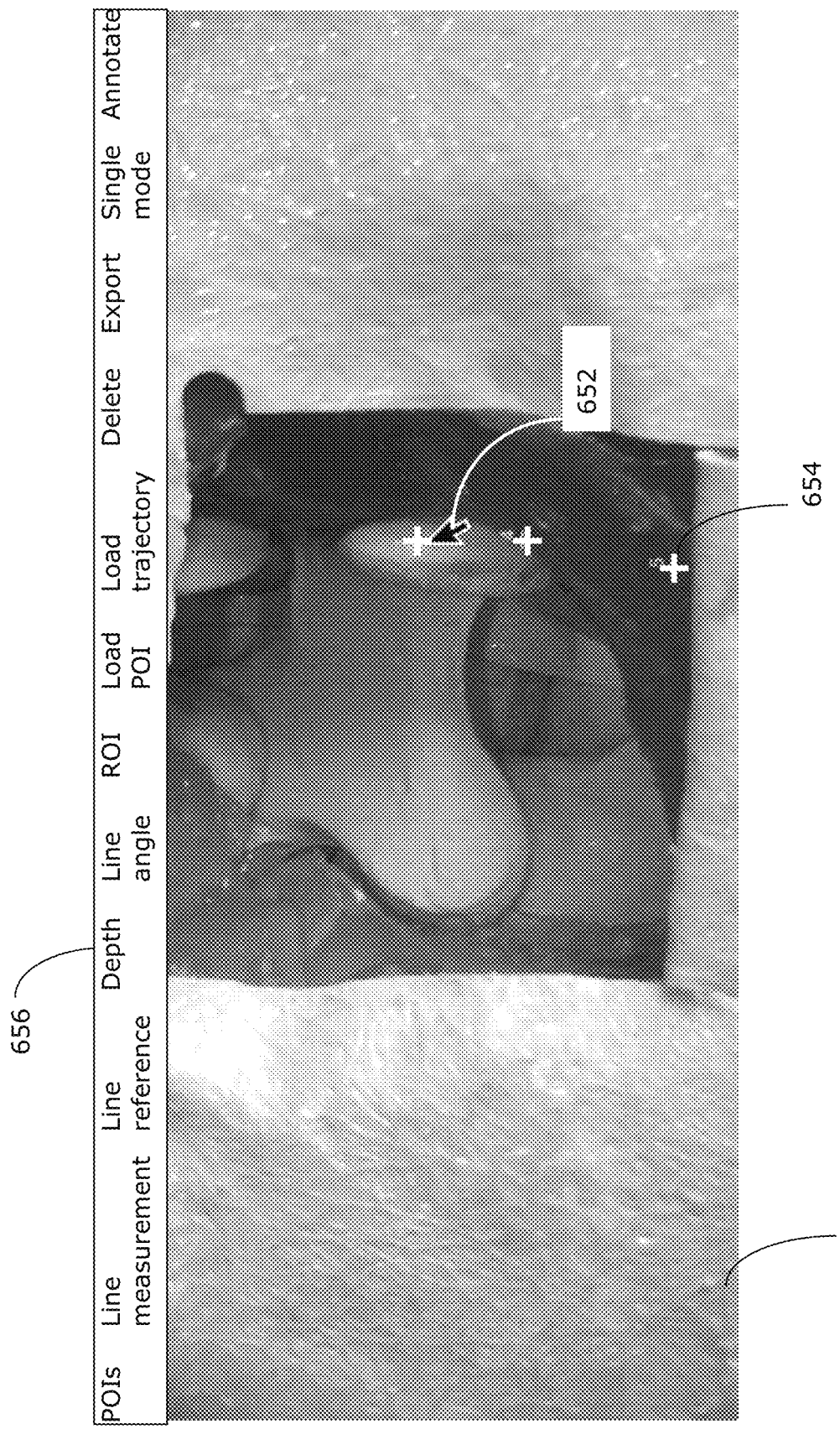
FIG. 6B shows an example display of a captured image including a cursor for interacting with the image.

In some examples, the 3D point may be selected by interacting with the display of the captured image. For example, the surgeon may move a cursor over the displayed image and click on a point on the image, or may touch a touch-sensitive display at a point on the image. FIG. 6B shows an example in which a cursor 652 is maneuvered in the displayed image 650. In the example shown, a menu 656 provides selectable options for selecting 3D points or reference lines. The surgeon may interact with the image 650 (e.g., clicking when the cursor 652 is at the desired location) to select a point 654 on the image 650. Because the displayed image 650 is a 2D image (i.e., having only x,y-coordinates), it may be assumed that the depth (i.e., z-coordinate) of the selected point 654 corresponds to the depth of the tissue displayed at the selected point 654. The depth of the tissue at any point may be determined using any suitable technique including, for example by obtaining a 3D scan of the tissue (e.g., using a 3D scanner 420) or by performing image analysis (e.g., by analyzing the focus depth at which the tissue is in focus). In some examples, the depth of the tissue may be determined from preoperative image data, such as MR or CT image data. In such cases, the depth of the selected point may correspond to deeper structures below the tissue surface, for example where the preoperative image data captures data about a structure (e.g., a tumor) below the tissue surface. Using the common coordinate space, the selected point 654 on the displayed image can be transformed to a 3D point in the tracking coordinate space. Thus, a point 654 that is selected by interacting with the displayed image 650 may be processed the same way as a point that is selected in 3D space by selection using a tracked pointing tool. For simplicity, the examples discussed below will refer to selection using a tracked tool in the tracking coordinate space. However, it should be understood that such examples may be similarly carried out using points selected by interacting with the displayed image, or a combination of selection methods.

In some examples, a single interaction may be used to select multiple 3D points or regions. For example, a single selection may be made to select all portions of the FOV corresponding to a characteristic of a selected point, such as the colour or depth indicated by the distal tip of the pointing tool.

The selected 3D point is stored in memory. In some examples, in addition to the 3D position of the 3D point, the orientation of the tracked tool is also stored. For example, the 3D position of the distal tip may be stored in association with the 3D orientation of the longitudinal axis of the pointing tool. The selected 3D point may thus be stored in associated with the selected 3D orientation.

In some examples, there may not be a selection of a 3D point and 606 may be omitted. In such cases, the following steps of the method 600 may be performed for the tracked real-time 3D position and/or orientation of the tracked tool. In some examples, even when a 3D point has been selected at 606, the method 600 may additionally be performed for the real-time 3D position and/or orientation of the tracked tool, for example as illustrated by examples discussed further below.

At 608, navigational information associated with the 3D position (and optionally orientation) of the tracked tool (and optionally the selected 3D point) is determined. In some examples, other sets of data (e.g., previously selected 3D points) may be used for determining the navigational information. In some examples, navigational information may be simply the 3D location and optionally orientation of the tracked tool (and optionally the selected 3D point) relative to the surgical site and the FOV of the camera.

At 610, a representation of the navigational information is displayed. This may involve the processor generating a virtual representation of the navigational information and outputting data to superimpose the virtual representation on the optical image captured by the camera. The virtual representation may be generated using the common coordinate space, so that the representation is superimposed on the optical image in a location of the image appropriate to the navigational information.

If no 3D point was selected (606 was omitted), the displayed navigational information may be navigational information related to the real-time 3D position (and optionally orientation) of the tracked tool. Navigational information related to the real-time 3D position and/or orientation may be a representation of the 3D position and/or orientation relative to the surgical site. Navigational information related to the real-time tracked position may be referred to as dynamic navigational information because it is dependent on real-time position of the tracked tool.

If a 3D point was selected at 606, the displayed navigational information may additionally or alternatively include navigational information calculated based on the selected 3D point. Navigational information related to a selected point may be referred to as static navigational information because it is dependent on a selected point that is not time-dependent. The displayed navigational information may include dynamic navigational information, static navigational information, and combinations thereof.

For example, the displayed representation of the navigational information may include a crosshair representing the projection of the distal tip of the tracked tool onto the surface of the surgical site. In another example, the displayed representation may include a line representing the longitudinal axis of the tracked tool.

In the example of FIG. 7A, the navigational information that is determined is the distance between two selected 3D points, as well as the location of the 3D points relative to the surgical site. The distance information may be determined by calculating the 3D distance between two selected 3D points, such as a currently selected 3D point 702 and an immediately previous selected 3D point 704.

In the example of FIG. 7A, the two 3D points 702, 704 are represented by two dots superimposed on the captured image 750, corresponding to the 3D position of the 3D points 702, 704 relative to the surgical site. The distance between the two 3D points 702, 704 is represented by a line between the two points 702, 704, and a label 706 indicating the distance.

In some examples, the distance may be calculated between one 3D point 702 and a predefined point (e.g., a predefined surgical target) instead of a previously selected 3D point. In some examples, the distance may be calculated between the 3D point 702 and a reference depth plane. A reference depth plane may be predefined (e.g., zero depth may be predefined as the surface of the patient's skin) or may be defined to be the depth of a previously selected 3D point. The orientation of the reference depth plane may be predefined or defined according to the orientation of the pointing tool, for example.

Figure 7B:
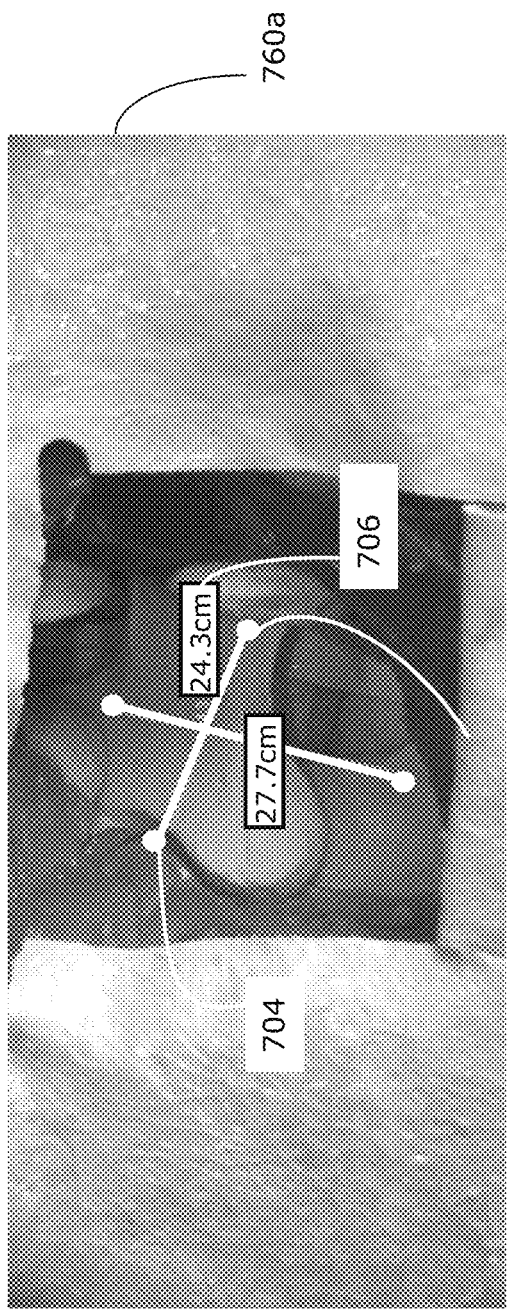
FIG. 7B shows example displays illustrating persistence of a visual representation of navigational information when the zoom level of the image changes.
Figure 7B:
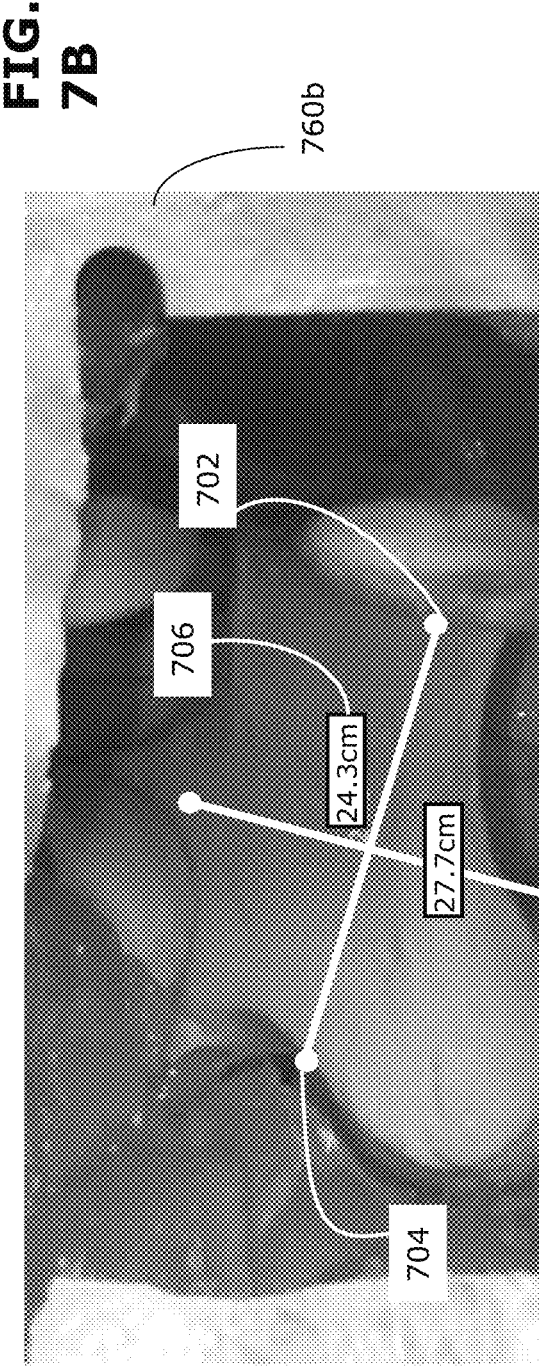
Figure 7C:
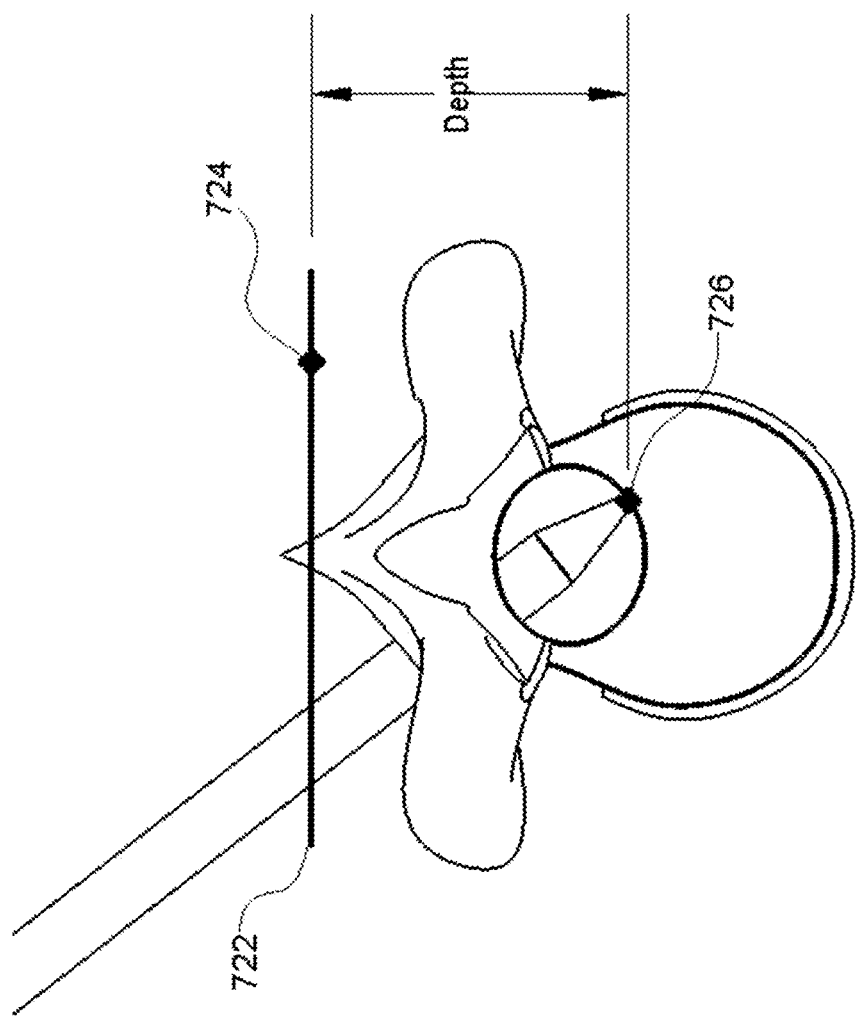
FIG. 7C illustrates how depth information may be calculated for a selected 3D point.

FIG. 7C illustrates an example, in the context of a spinal procedure, of how a reference depth plane 722 may be defined by a previously selected 3D point 724, and the navigational information may be the depth of a currently selected 3D point 726 relative to the reference depth plane 722 (e.g., calculated as a perpendicular distance from the reference depth plane 722).

In some examples, instead of a selected 3D point 702, the distance or depth may be calculated between a previously selected 3D point 704 (or a reference point or plane) and the real-time 3D position of the tracked tool (in this example the distal tip of a pointing tool).

Other navigational information that may be calculated include, for example, angle measurements between two orientations (e.g., between a selected 3D orientation and a planned trajectory line, between two selected 3D orientations, or between a selected 3D orientation and a real-time tracked 3D orientation).

Such visuospatial information may be useful for collection of anatomic measurements in real-time (e.g., disc space height/depth or relative angle of vertebral endplates during a spinal procedure), and for determining changes in such anatomic measurements during the procedure (e.g., in discectomy and distraction). Calculation and display of this information based on selection by a pointing tool may simplify the procedure and may provide more accurate information, compared to conventional techniques (e.g., physically placing a rule on the target area or using X-ray imaging to confirm desired anatomic corrections).

At 612, the displayed representation is updated when: the 3D position and orientation of the tracked tool changes (614); and/or when the FOV of the camera changes (616).

614 may be carried out where the navigational information is dynamic navigational information dependent on the real-time tracking of the tracked tool. For example, updating the displayed dynamic navigational information may include performing 602, 604 and 608 to track the object and calculate navigational information as the object moves, and then displaying the updated navigational information. The updated navigational information may be an updated representation of the 3D position and/or orientation of the tracked tool relative to the surgical site. For example, distance or depth relative to a reference point or plane may be calculated and updated in real-time as the tracked tool moves. Other examples will be discussed further below.

616 may be carried out for both dynamic and static navigational information, to reflect the changed FOV and to maintain spatial persistence of the representation in the changed FOV. Changes in the FOV of the camera may be determined by the tracking information from the tracking system (e.g., in examples where the camera is tracked by the tracking system), by information from a positioning system that positions the camera (e.g., in examples where the camera is supported by a robotic arm) and/or by information from the camera itself (e.g., the camera may provide information indicating the zoom level of the captured image). Because the 3D point, surgical site and the captured image are all mapped to the common coordinate space, the visual representation can be updated by the processor.

In some examples, updating of the displayed representation may also be performed at fixed time intervals (e.g., every 100 ms) or in response to user input. Thus, an update (or refresh) of the displayed representation may occur even where there is no movement of the tracked tool and no change in FOV of the camera.

Figure 9A:
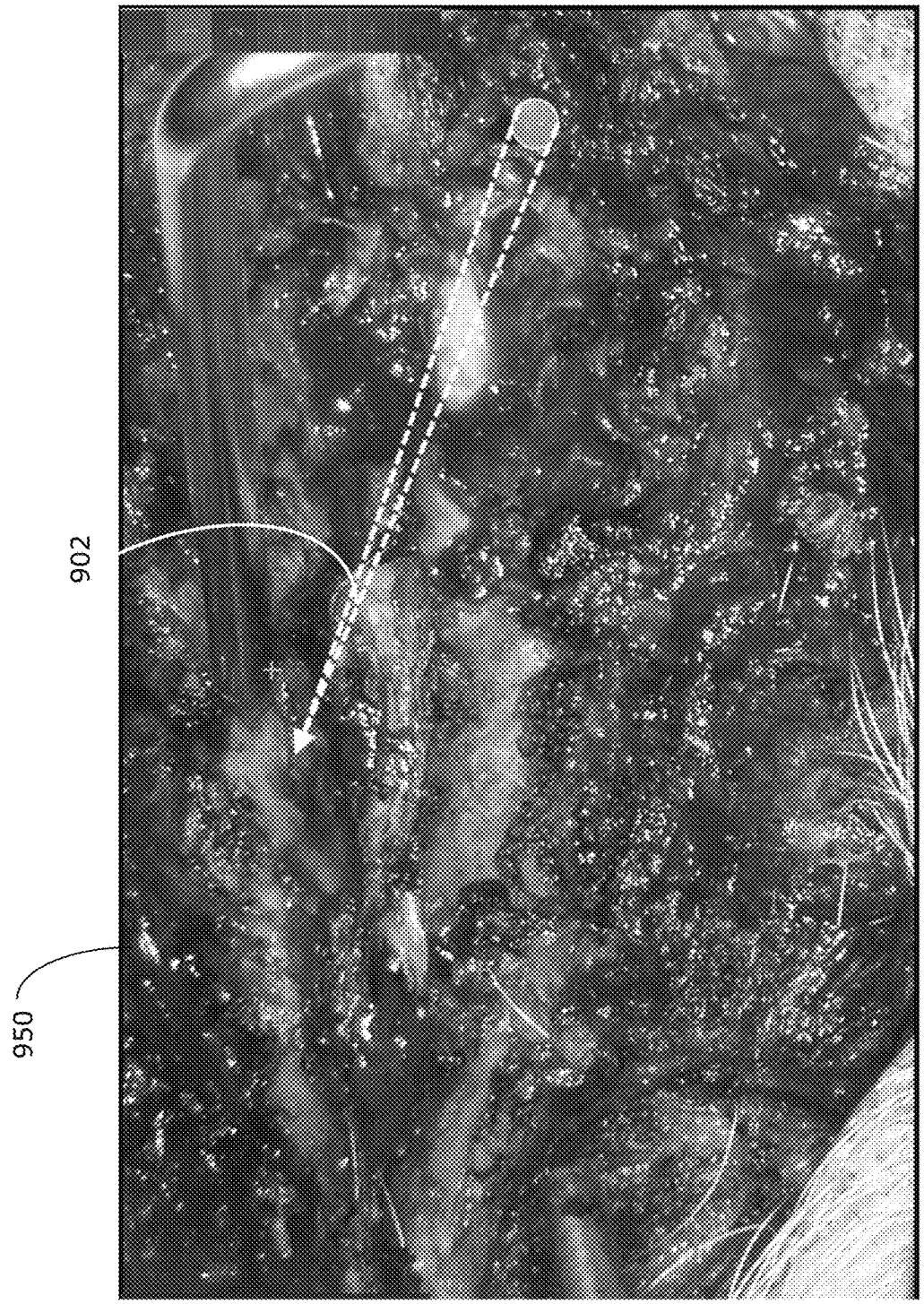
FIG. 9A shows an example display of a captured image including visual representation of a selected 3D point and 3D orientation.
Figure 9C:
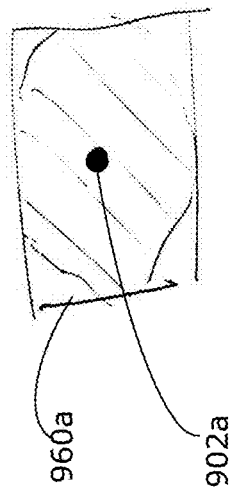
FIGS. 9B-9G illustrate an example of how selected 3D points and orientations are provided as visuospatial information.
Figure 9E:
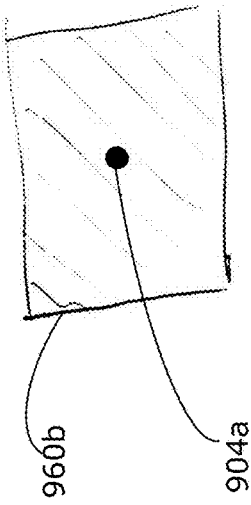

In the example of FIG. 7A, when the FOV changes, the representation of the 3D points 702, 704 is updated to accurately depict the 3D position of the 3D points 702, 704 within the new FOV. An example is illustrated in FIGS. 9B-9G (discussed in greater detail below), where selected points shown in FIGS. 9C and 9E are persistent even when the viewpoint changes in FIG. 9G. Where the orientation and/or the zoom level of the camera changes, the visual representation of the distance between the points 702, 704 may change (e.g., visually lengthened when the zoom level increases), however because the actual physical distance between the points 702, 704 is unchanged the distance indicated by the label 706 is unchanged. An example of this is shown in FIG. 7B. In one image 760a, the image is shown at a first zoom level, including visual representation of 3D points 702, 704 and a label 706 indicating the actual distance between the points 702, 704. When the zoom level is increased to the second image 760b, the visual representation of the 3D points 702, 704 and the distance between them is accordingly also zoomed, however the actual distance indicated by the label 706 is unchanged. The processor may perform calculations to update the visual representation in accordance with the changed FOV, but the processor does not need to recalculate the 3D position of the points 702, 704 or the navigational information (in this case, the distance between the points 702, 704) because no changes have been made to the physical position and orientation of the selected 3D points.

In some examples, the orientation as well as position of the 3D point may be determined and stored. The visual representation of the selected 3D point may include information indicating the selected 3D orientation of the tracked tool. For example, FIG. 9A shows an image in which the selected 3D point is represented as an arrow superimposed on the captured image 950, where the tip of the arrow 902 represents the position of the selected 3D point, and the body of the arrow corresponds to the selected 3D orientation.

Figure 9G:
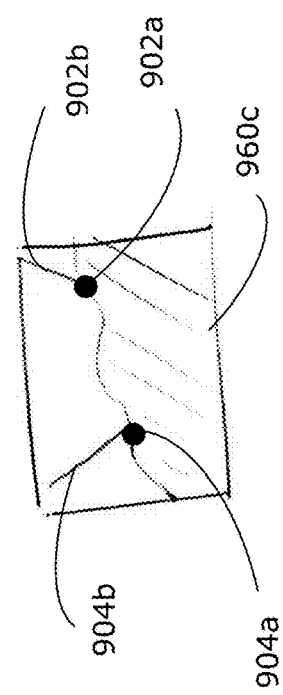
Figure 9B:
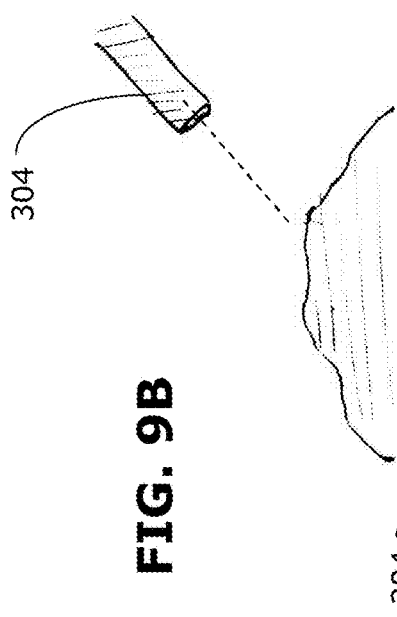
Figure 9D:
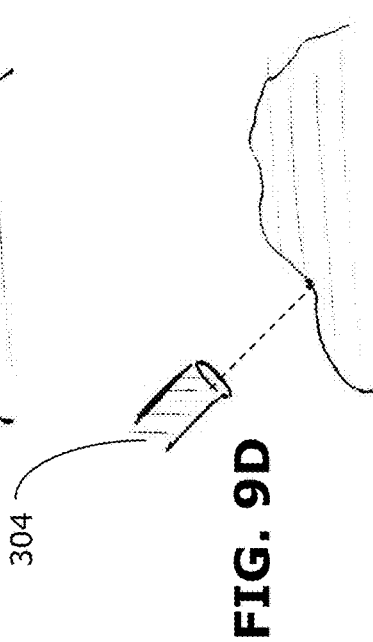
Figure 9F:
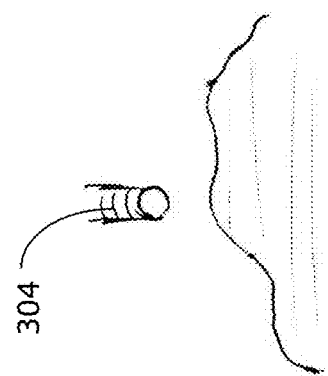

FIGS. 9B-9G illustrate an example of how selected 3D points and associated 3D orientations are provided as visuospatial information. FIGS. 9B-9G also illustrate an example in which a 3D point may be selected without the use of a tracked tool. In FIGS. 9B-9G, a 3D point may be selected as the center of the captured image, and the associated 3D orientation may be the normal to the plane of the captured image. In FIGS. 9B and 9C, a first 3D point 902a is selected (e.g., by activation of an input mechanism such as a foot pedal) when the FOV of the camera (e.g., an topical scope 304) is at a first position and orientation (indicated by dotted line), corresponding to the captured image 960a shown in FIG. 9C. In FIGS. 9D and 9E, a second 3D point 904a is selected in a similar way when the FOV of the camera is at a second position and orientation (indicated by dotted line), corresponding to the captured image 960b shown in FIG. 9E. The 3D positions and associated orientations are stored. In FIGS. 9F and 9G, the camera again changes FOV to capture a side view of the surgical site, corresponding to the captured image 960c shown in FIG. 9G. In FIG. 9G, the first and second 3D points 902a, 904a are superimposed on the captured image. Further, the 3D orientation associated with the stored points are represented as axes 902b, 904b.

Figure 8:
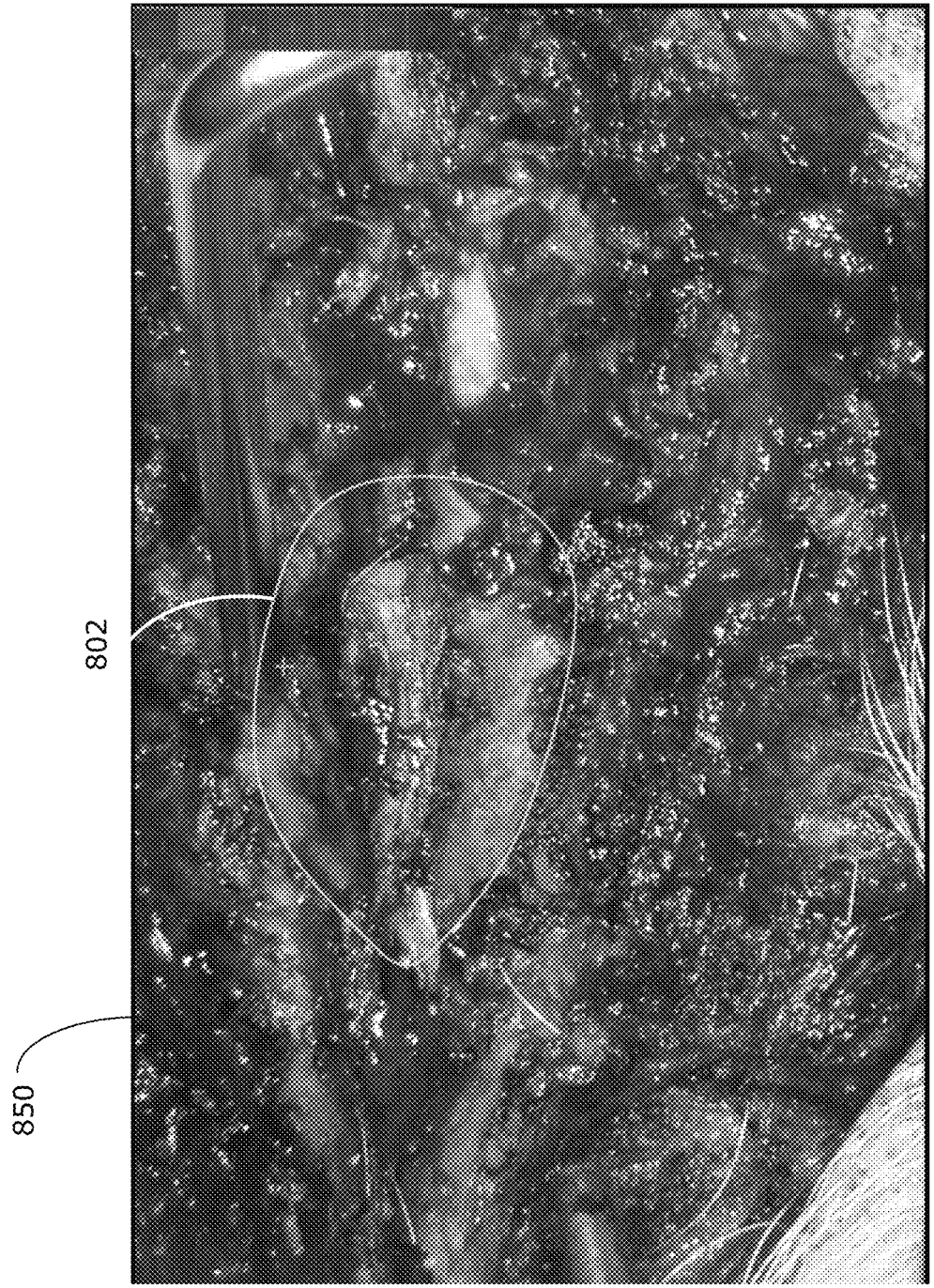
FIG. 8 shows an example display of a captured image including visual representation of a selected boundary of interest.

FIG. 8 illustrates another example of visuospatial information that may be provided as feedback during a medical procedure. In this example, a plurality of 3D points may be selected in order to form a boundary of interest (BOI) 802. The BOI may be defined by connecting the 3D points along the shortest path between points (e.g., creating a closed polygon shape), or may be defined by performing a spline interpolation of the points (e.g., to obtain a smoother BOI), for example. The BOI may further define a region of interest (ROI), as discussed further below. The plurality of 3D points may be selected by the surgeon positioning the pointing tool at different locations and activating the input mechanism at each location. The plurality of 3D points may also be selected by the surgeon maintaining activation of the input mechanism (e.g., keeping a button or foot pedal depressed) while moving the pointing tool to "draw" the boundary in 3D space. The 3D position of the distal tip of the pointing tool may be sampled at regular intervals while the input mechanism is activated, to obtain a set of 3D points that is used to define the BOI. To assist in selection of points for the BOI, the display may be updated with a visual representation of the 3D points as they are selected.

Figure 10:
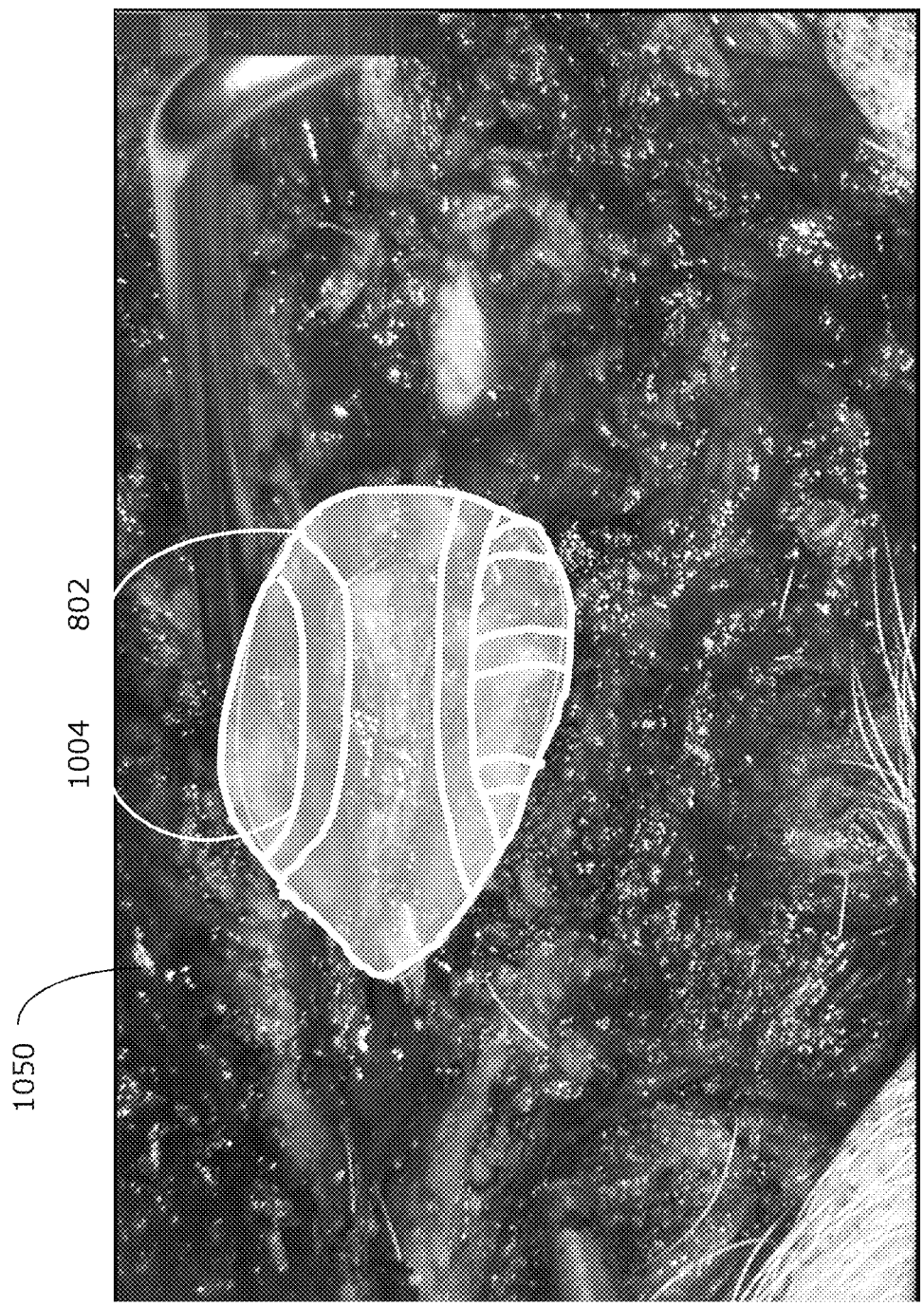
FIG. 10 shows an example display of a captured image including navigational information within a selected region of interest.

A visual representation of the BOI 802 may be superimposed on the captured image 850, as discussed above. Navigational information associated with the BOI 802 may include imaging data obtained prior to or during the procedure. For example, the navigational information may include pre-operative and/or intra-operative imaging such as ultrasound, or 3D imaging of blood vessels or nervous structures. Through the use of a common coordinate space (e.g., using transformation mapping as discussed above), the portion of pre-surgical imaging data that corresponds to the ROI defined by the BOI 802 may be identified and extracted. The imaging data 1004 that is provided as visuospatial information overlaid on the captured image 1050 may thus be limited to the ROI defined by the BOI 802, as shown in FIG. 10. This may reduce the cognitive load on the surgeon by presenting only navigational information that is relevant to the ROI.

Figure 12:
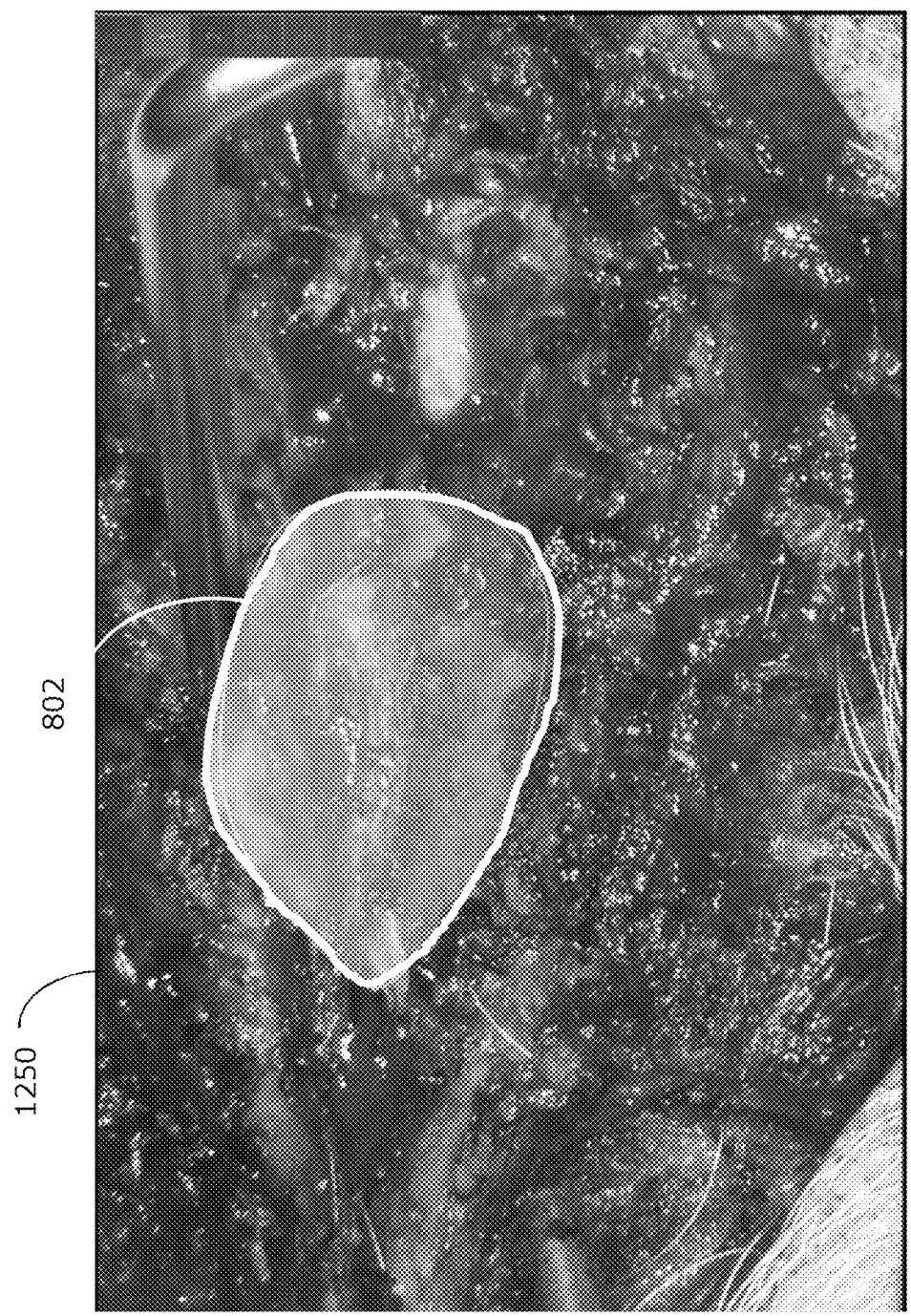
FIG. 12 shows an example display of a captured image including visual modification within a selected region of interest.

FIG. 12 illustrates another example in which the visual representation of the ROI defined by the BOI 802 is modified. Here, modification to the image characteristics of the ROI (e.g., brightness, hue and/or saturation) is made to the captured image 1250. For example, the ROI may be modified to remove redness, so that the site can be better viewed without being obscured by blood. By limiting such modification to the ROI, rather than the entire captured image 1250, the processing load on the processor may be decreased and performance may be improved. In some examples, the visual modification may include an automatic change to the position, orientation and/or zoom level of the camera so that the ROI is kept within the FOV.

In some examples, feedback may be provided to indicate whether a tracked tool (e.g., surgical tool) is within, on or outside of the BOI 802. For example, in a training context, a trainer may select a BOI 802 to define the region within which a trainee should operate. If the trainee moves the tracked surgical tool out of the BOI 802, feedback (e.g., an audio cue) may be provided to warn the trainee to stay within the BOI 802.

Figure 11:
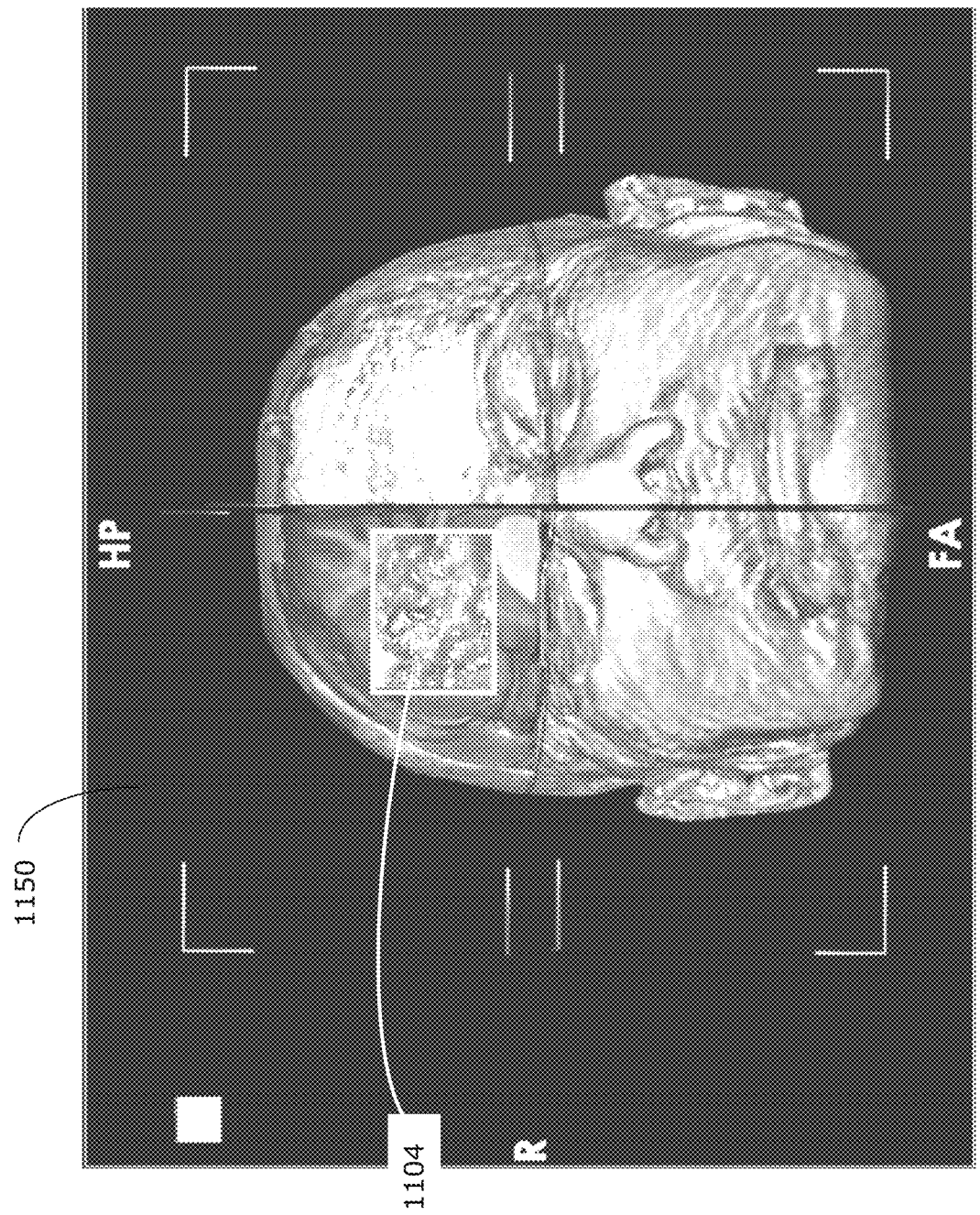
FIG. 11 shows an example display of imaging data including an overlay of real-time captured images in a selected region of interest.

In some examples, the visuospatial feedback may be provided as an overlay of the real-time optical image superimposed on imaging data, for example as shown in FIG. 11. In this example, the portion of imaging data (in this case, an intra-operative 3D scan 1150 of the surface of the patient's head) corresponding to a selected ROI (or corresponding to the vicinity of a selected 3D point) is identified, using the common coordinate space. The identified portion of imaging data is then overlaid with a portion of the real-time optical image 1104 corresponding to the selected ROI (or vicinity of the selected 3D point). It should be noted that the intra-operative 3D scan 1150 is oriented to match the orientation of the optical image 1104, based on mapping to the common coordinate space.

Figure 13:
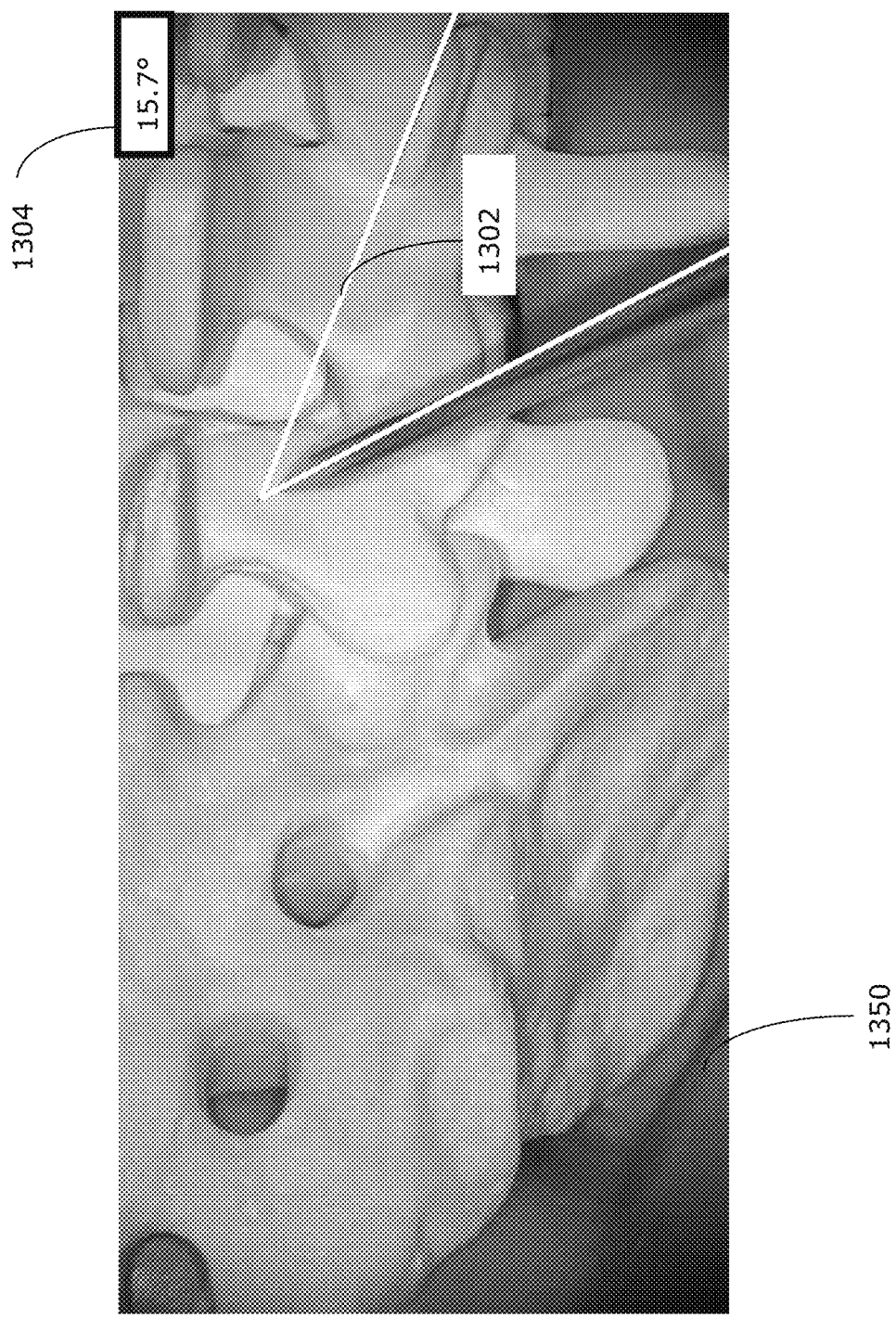
FIG. 13 shows an example display of a captured image including visual representation of selected reference lines.

FIG. 13 illustrates an example in which the feedback provided is in the form of reference lines 1302 superimposed on the captured image 1350. A reference line 1302 may be defined by connecting between two selected 3D points, in a manner similar to how a BOI is defined. A reference line 1302 may additionally or alternatively be defined by a selected 3D orientation (e.g., defined by the longitudinal axis of the tracked tool). The reference lines 1302 may be used, for example, to align screws in lumbar fusion surgery. It should be noted that the reference line 1302 may also be dynamic, that is the reference line 1302 may be defined by the real-time orientation of the tracked tool. Further navigational information that may be represented may be an angle measurement 1304 between two reference lines.

Figure 14:
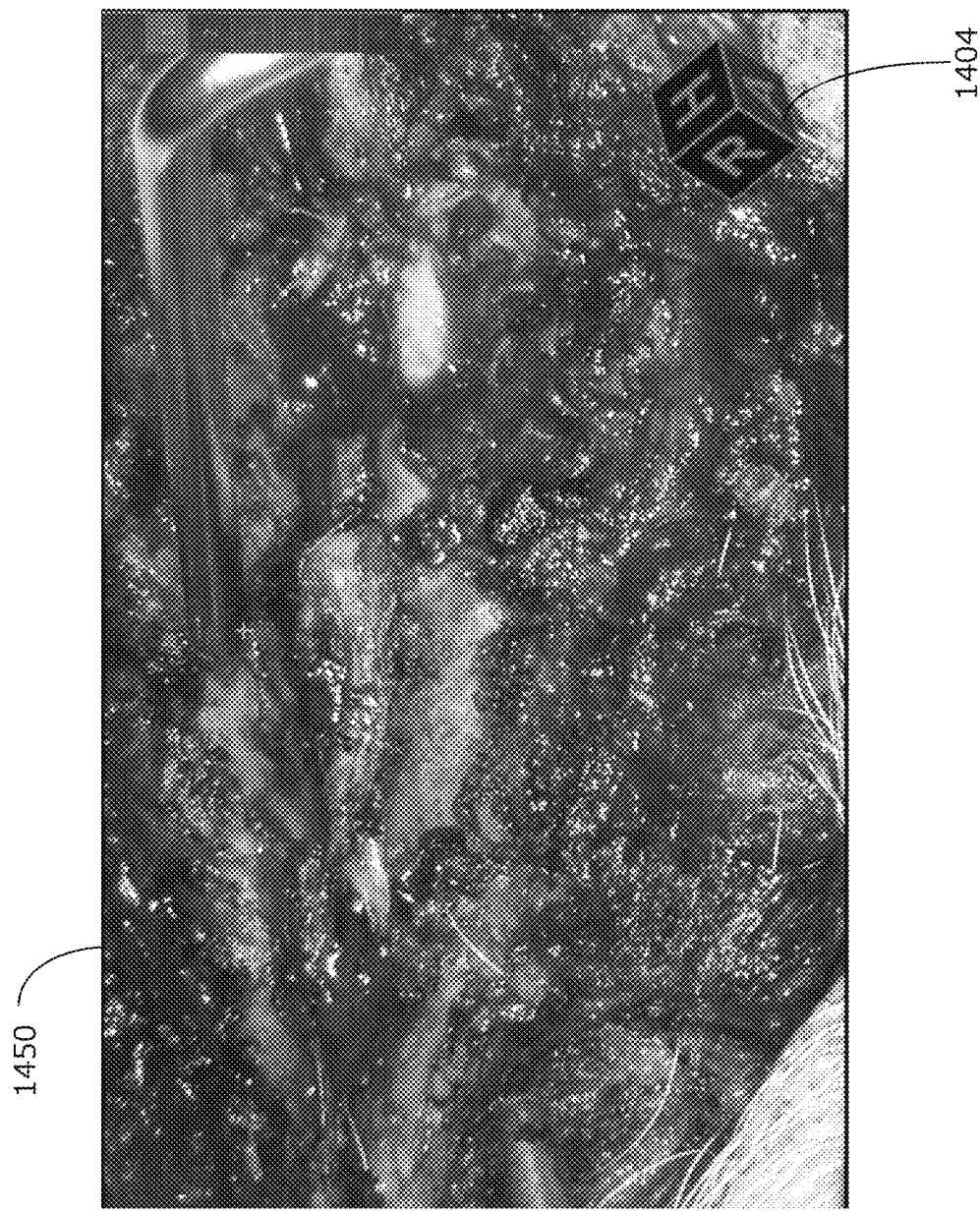
FIG. 14 shows an example display of a captured image including a visual representation of a reference orientation.

FIG. 14 illustrates an example in which the navigational information is provided as a visual representation (in this case a cube 1404) of the orientation of the captured image 1450 relative to a reference orientation (e.g., the patient's anatomical orientation). The cube 1404 may show symbols indicating orientation directions. For example, the cube 1404 may show "H" for head, "R" for right and "A" for anterior. As the orientation of the FOV changes, the cube 1404 also changes to represent the corresponding reference orientation.

In some examples, navigational information may be based on information extracted from planning information. Planning information may include information defining a planned trajectory and/or identification of one or more planned targets or reference points. Such pre-surgical planning may be carried out using pre-surgical imaging data, and defined in the imaging data coordinate space. Using transformation to the common coordinate space, the planning information may be provided as visuospatial information overlaid on the captured image. Points or regions of interest may also be selected, pre-operatively or intra-operatively, in the imaging data coordinate space (e.g., by interacting with a displayed MRI image) and similarly correlated to the captured image.

Figure 15:
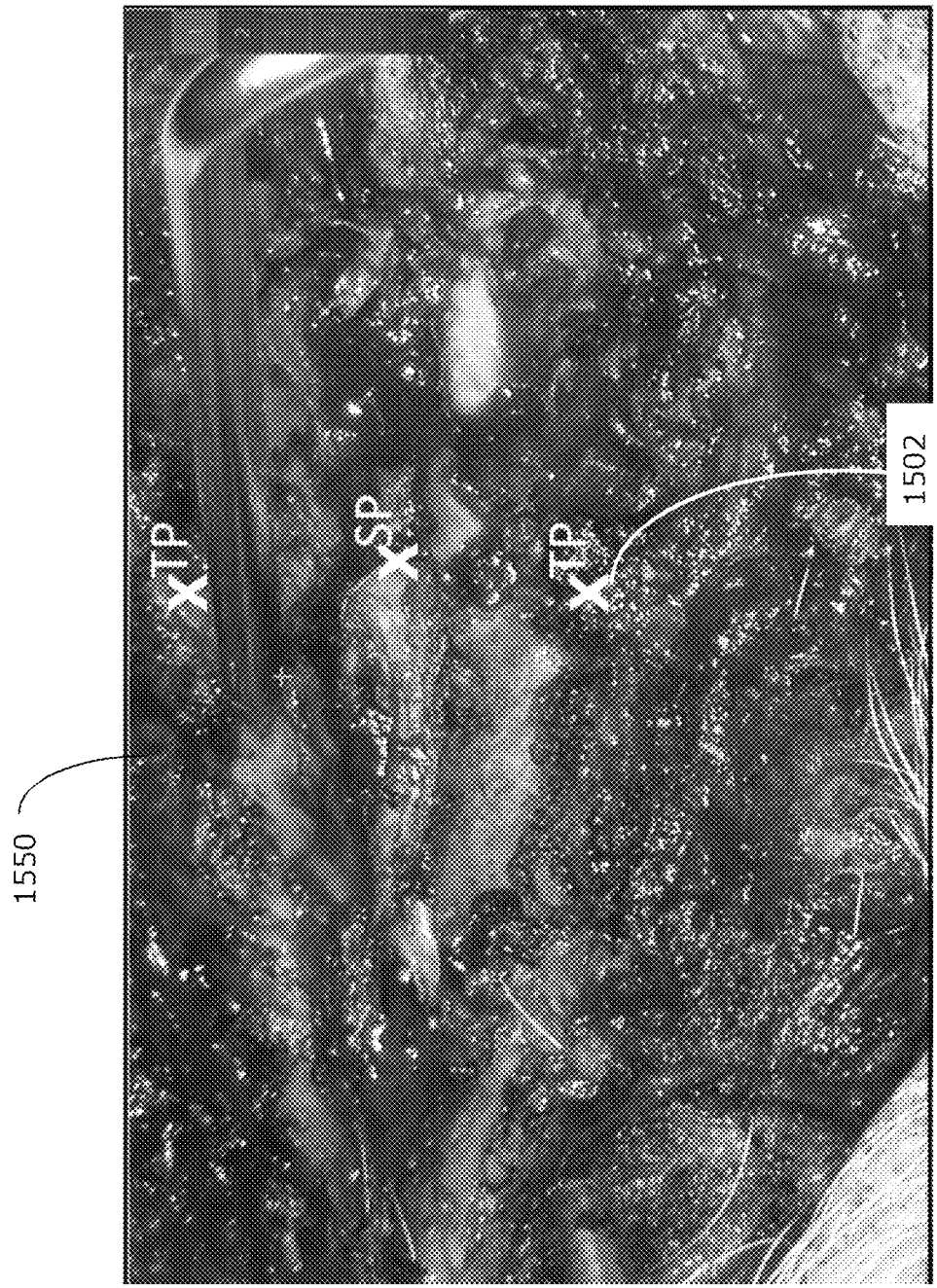
FIG. 15 shows an example display of a captured image including visual representation of planned targets.

An example of this is shown in FIG. 15. Here, points 1502 identified in the imaging data coordinate space are superimposed on the captured image 1550. The identified points 1502 may be labelled according to labels defined in planning information. In some examples, the identified points 1502 may be labelled according to user input (e.g., the surgeon may select or enter a label for a point when a 3D point is selected). In this example, the points 1502 are labelled as "TP" for transverse process and "SP" for spinous process. In another example, a planned trajectory may be displayed as an arrow or path overlaid on the captured image 1550. This visual feedback may be combined with other visual modifications, such as changes in colour and/or size to indicate whether a tracked tool is correctly positioned or aligned with the planned trajectory/target. The visual feedback may also be combined with other feedback modalities, such as audio cues to indicate if the tracked tool is properly positioned or aligned. By providing planning information in situ as visuospatial feedback, performance error may be reduced.

Figure 16:
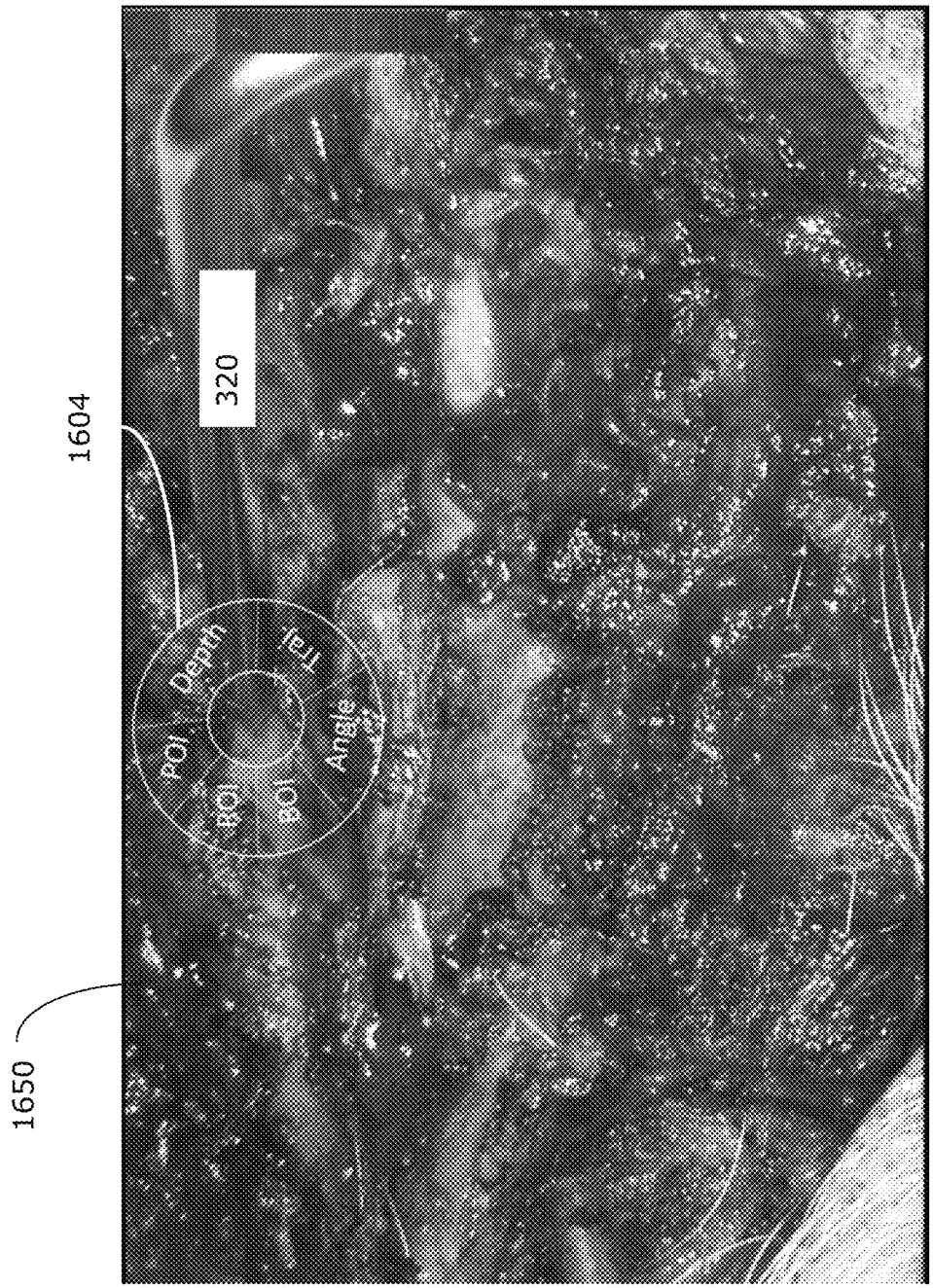
FIG. 16 shows an example display of a captured image including an overlay of a user interface.

FIG. 16 illustrates an example of a user interface 1604 that may be presented, to enable the surgeon to interact with a navigation system using a tracked tool 320 (in this example, a pointing tool). The user interface 1604 may be presented as a radial menu overlaid on the captured image 1650 and centered about the tracked tool. Icons in the radial menu may be selected to control various aspects of the navigation system, for example to change a zoom level of the optical camera, to change the type of visuospatial information presented and/or to cause display of other information on another display. By changing the orientation of the tracked tool and without moving the distal point of the tool, the surgeon may select a particular icon in the user interface 1604. This may enable the surgeon to more easily provide input to the navigation system, without having to change to a different display or otherwise remove attention from the surgical site.

It should be understood that the various examples of visuospatial information described above may be provided in combination. In some examples, it may be possible to switch between different displays of visuospatial information. It may be possible to select whether or not to display certain selected 3D point(s), BOI(s) and/or reference line(s), and 3D point(s), BOI(s) and/or reference line(s) may be selectively deleted or removed from memory.

In some examples, selection of a 3D point may be performed with a tool other than a pointing tool. For example, any tracked surgical tool may be used to select a 3D point. In another example, when a selection input is made and there is no tracked tool within the FOV of the camera, the center of the captured image may be selected by default, and the selected orientation may be the normal to the plane of the captured image by default. As well, selection of a 3D point may be performed through interaction with a displayed optical image, or through interaction with other imaging data.

Further, selection of a 3D point may not be required for navigational information to be calculated and displayed. The navigational information may be calculated and displayed based only on the real-time tracked position and orientation of the tracked tool.

Figure 17:
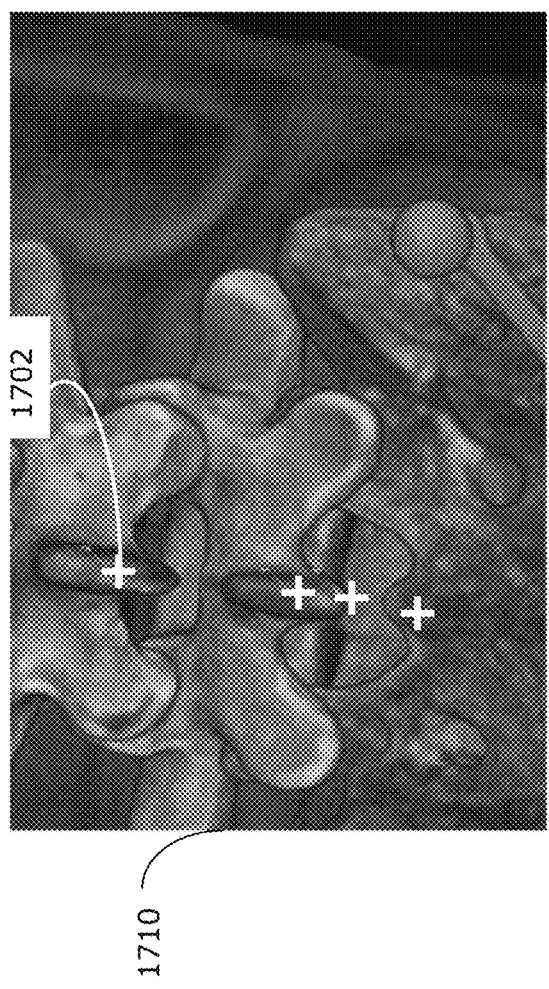
FIG. 17 shows example displays of different image modalities, illustrating persistence of visual representation of navigational information across different image modalities.
Figure 17:
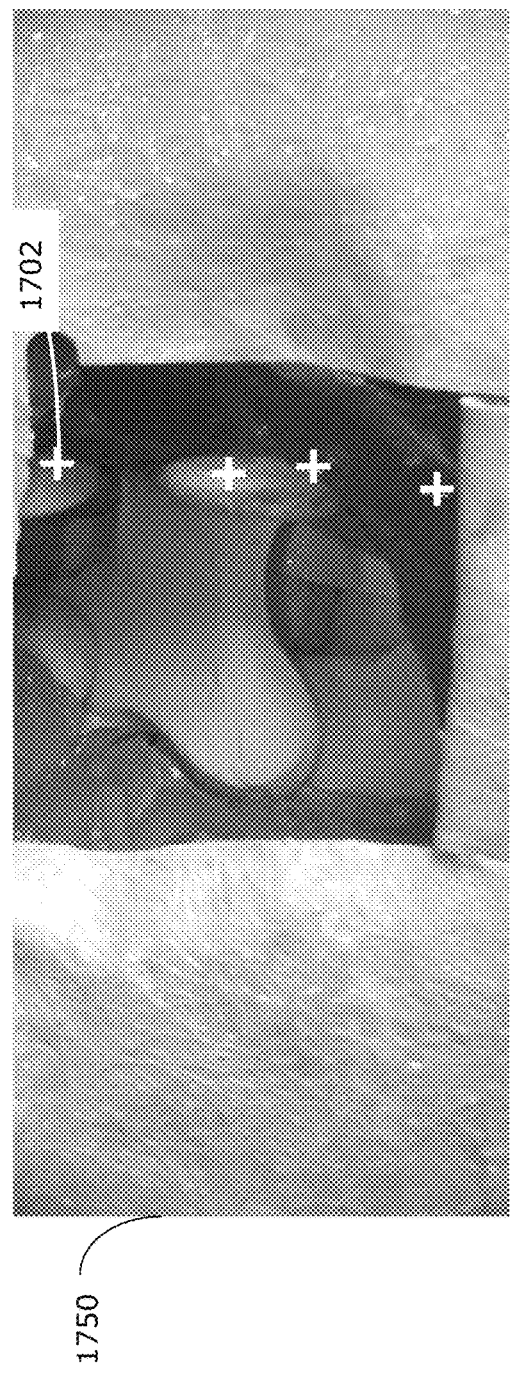

In some examples, navigational information associated with the real-time tracked position and orientation, selected 3D point(s), defined BOI(s) and/or reference line(s) may be presented using other feedback modalities, including tactile feedback and audio feedback, for example. The selected 3D point(s), defined BOI(s) and/or reference line(s) point may also be represented in other visual feedback modalities. For example, the selected 3D point(s), defined BOI(s) and/or reference line(s) may also be displayed as a visual overlay on a 3D scan or in an MRI image. Similarly, 3D point(s), defined BOI(s) and/or reference line(s) that are selected in other modalities (e.g., through interacting with an image of a 3D scan or an MRI image) may also be displayed as a visual overlay in the captured optical image. In this way, the present disclosure provides spatial persistence not only within a single feedback modality, but also spatial persistence across multiple imaging modalities. FIG. 17 shows an example in which the visual representation of the navigational information is persistent across different image modalities. In this example, visual representation of selected 3D points 1702 is persistent between a preoperative image 1710 and the real-time optically captured image 1720.

Notably, the locations of the selected 3D points 1702 are spatially persistent across the different images 1710, 1720.

In various examples disclosed herein, the present disclosure provides navigational information to the surgeon in the context of the displayed optical image. The surgeon is not required to switch tools (e.g., use a physical rule to measure distances), refer to another interface (e.g., refer to a separate screen showing navigational information) or otherwise interrupt the procedure in order to access navigational information. Although examples above describe using a pointing tool as the tracked tool, any tool held in the surgeon's hand may serve as the tracked tool. For example, the distal tip of any tool (e.g., where the distal tip position has been determined relative to the tracked tool, via calibration) may be used similar to the distal tip of the pointing tool. Thus, the surgeon is able to access more information while keeping the same tool held in the hand.

Further, by providing the navigational information displayed on the optical image, other personnel in the operating room may be able to view the navigational information, for example for training purposes. The optical image with superimposed navigational information may also be stored for future use (e.g., for quality assurance purposes).

It should be understood that the captured optical images in the various examples described above may be real-time video images.

Although the above discussion refers to the surgeon as being the user who controls and uses the examples of the present disclosure, it should be understood that the present disclosure is not limited to any specific user. In some examples, there may be a plurality of users involved.

While some embodiments or aspects of the present disclosure may be implemented in fully functioning computers and computer systems, other embodiments or aspects may be capable of being distributed as a computing product in a variety of forms and may be capable of being applied regardless of the particular type of machine or computer readable media used to actually effect the distribution.

At least some aspects disclosed may be embodied, at least in part, in software. That is, some disclosed techniques and methods may be carried out in a computer system or other data processing system in response to its processor, such as a microprocessor, executing sequences of instructions contained in a memory, such as read-only memory (ROM), volatile random access memory (RAM), non-volatile memory, cache or a remote storage device.

A computer readable storage medium may be used to store software and data which when executed by a data processing system causes the system to perform various methods or techniques of the present disclosure. The executable software and data may be stored in various places including for example ROM, volatile RAM, non-volatile memory and/or cache. Portions of this software and/or data may be stored in any one of these storage devices.

Examples of computer-readable storage media may include, but are not limited to, recordable and non-recordable type media such as volatile and non-volatile memory devices, ROM, RAM, flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Furthermore, at least some of the methods described herein may be capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

At least some of the elements of the systems described herein may be implemented by software, or a combination of software and hardware. Elements of the system that are implemented via software may be written in a high-level procedural language such as object oriented programming or a scripting language. Accordingly, the program code may be written in C, C++, J++, or any other suitable programming language and may comprise modules or classes, as is known to those skilled in object oriented programming. At least some of the elements of the system that are implemented via software may be written in assembly language, machine language or firmware as needed. In either case, the program code can be stored on storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

While the teachings described herein are in conjunction with various embodiments for illustrative purposes, it is not intended that the teachings be limited to such embodiments. On the contrary, the teachings described and illustrated herein encompass various alternatives, modifications, and equivalents, without departing from the described embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

The invention claimed is:

1. A system for providing feedback during a medical procedure, the system comprising:
   a tracking system configured to obtain tracking information about three-dimensional (3D) position and orientation of a tracked tool during the medical procedure;
   the tracked tool coupled to tracking markers to enable tracking of the tracked tool by the tracking system;
   a camera for capturing an optical image of a field-of-view (FOV) of a site and the tracked tool during the medical procedure;
   a display for displaying the optical image of the FOV; and
   an input mechanism for indicating selection of one or more virtual 3D points in the optical image of the FOV, the input mechanism being part of the tracked tool;
   a processor coupled to receive input data from the tracking system, the input mechanism, and the camera, and coupled to transmit output data for display on the display, the processor being configured to:

determine the 3D position and orientation of the tracked tool, relative to the site, based on the tracking information;
receive selection of one or more 3D points from the input mechanism based on the 3D position and orientation of the tracked tool;
map the 3D position and orientation of the tracked tool and the one or more selected 3D points to a common coordinate space, to determine the 3D position and orientation of the tracked tool and the one or more selected 3D points relative to the FOV;
determine navigational information associated with the 3D position and orientation of the tracked tool and the one or more selected 3D points, the navigational information including a measurement of distance or angle, wherein determining navigational information comprises determining a measurement between the 3D position and orientation of the tracked tool to a reference defined by at least one of the one or more selected 3D points in the site;
cause the display to display a virtual representation of the navigational information overlaid on the FOV of the site and the tracked tool, the navigational information being displayed as an indication of the measurement overlaid on the FOV; and
update the displayed virtual representation by:
when the 3D position and orientation of the tracked tool changes, updating the displayed virtual representation of the one or more selected 3D points in accordance with the changed 3D position and orientation of the tracked tool; or
when the FOV changes, updating the displayed virtual representation of the one or more selected 3D points to follow the changed FOV.

2. The system of claim 1, wherein the tracking system is further configured to:
track position and orientation of the camera or a support of the camera; and
track position and orientation of the site;
wherein the processor is further configured to:
map between the 3D position and orientation of the tracked tool, the site and the FOV, using information from the tracking system; and
cause the display to update the displayed virtual representation to follow the changed FOV, based on mapping between the 3D position and orientation of the tracked tool, the site and the FOV, using information from the tracking system.

3. The system of claim 2, wherein the processor is further configured to:
determine an orientation of the camera relative to a reference orientation, using information from the tracking system; and
cause the display to display information overlaid on the FOV indicating the orientation of the FOV relative to the reference orientation.

4. The system of claim 1, wherein the processor is configured to:
receive selection of multiple 3D points indicated by the tracked tool;
determine a region of interest (ROI) based on the selected multiple 3D points;
determine navigational information associated with the ROI; and
cause the display to display a virtual representation of the ROI overlaid on the FOV, the virtual representation including the navigational information.

5. The system of claim 4, wherein the navigational information comprises imaging data of the ROI, wherein the overlay on the FOV includes the imaging data only for the ROI.

6. The system of claim 4, wherein the processor is further configured to modify visual display of the optical image of the FOV within the ROI.

7. The system of claim 1, wherein the processor is further configured to:
receive selection of multiple 3D points indicated by the tracked tool;
determine a boundary of interest (BOI) based on the selected multiple 3D points;
cause the display to display a virtual representation of the BOI overlaid on the FOV; and
cause output of feedback indicating position and orientation of another tracked tool relative to the BOI.

8. The system of claim 4, wherein the processor is further configured to:
determine navigational information by determining orientation of a longitudinal axis of the tracked tool; and
cause the display to display a virtual representation of the navigational information as a reference line overlaid on the FOV.

9. The system of claim 1, wherein the measurement is a measurement of the distance between the 3D position of the tracked tool and the at least one of the one or more selected 3D points.

10. The system of claim 1, wherein the at least one of the one or more selected 3D points defines part of a reference line, and the measurement is a measurement of an angle between the 3D orientation of the tracked tool and the reference line.

11. The system of claim 1, wherein the at least one of the one or more selected 3D points defines part of a reference depth plane, and the measurement is a measurement of a depth difference between the 3D position of the tracked tool and the reference depth plane.

12. The system of claim 1, wherein the processor is further configured to:
receive planning information defining a planned trajectory or planned target;
wherein the navigational information is extracted from the planning information and displayed in association with the 3D position and orientation of the tracked tool overlaid on the FOV.

13. The system of claim 1, wherein the processor is further configured to:
cause the display to display a virtual representation of the 3D position and orientation of the tracked tool overlaid on a display of imaging data.

14. The system of claim 13, wherein the processor is further configured to:
cause the display to display a portion of the FOV, corresponding to the 3D position and orientation of the tracked tool, overlaid on the imaging data.

15. The system of claim 1, wherein the system comprises an additional input mechanism for selecting an additional virtual 3D point via user interaction with the displayed FOV, and wherein the processor is further configured to:
receive selection of the additional virtual 3D point via user interaction with the displayed FOV.

16. A method for providing feedback during a medical procedure, the method comprising:
determining a 3D position and orientation of a tracked tool, relative to a site of the medical procedure, based on tracking information received from a tracking system that is tracking the tracked tool;

receiving selection of one or more 3D points from an input mechanism based on the 3D position and orientation of the tracked tool, the input mechanism being part of the tracked tool;

mapping the 3D position and orientation of the tracked tool and the one or more selected 3D points to a common coordinate space, to determine the 3D position and orientation of the tracked tool and the one or more selected 3D points relative to a field- of-view (FOV) of a camera that is capturing an optical image of the site and the tracked tool;

determining navigational information associated with the 3D position and orientation of the tracked tool and the one or more selected 3D points, the navigational information including a measurement of distance or angle, wherein determining navigational information comprises determining a measurement between the 3D position and orientation of the tracked tool to a reference defined by at least one of the one or more selected 3D points in the site;

causing a display to display a virtual representation of the navigational information overlaid on the FOV of the site and the tracked tool, the navigational information being displayed as an indication of the measurement overlaid on the FOV; and updating the displayed virtual representation by:
  when the 3D position and orientation of the tracked tool changes, updating the displayed virtual representation of the one or more selected 3D points in accordance with the changed 3D position and orientation of the tracked tool; or
  when the FOV changes, updating the displayed virtual representation of the one or more selected 3D points to follow the changed FOV.

17. The system of claim 1, wherein the one or more selected 3D points are stationary relative to the site.

* * * * *

UNITED STATES PATENT AND TRADEMARK OFFICE
CERTIFICATE OF CORRECTION

| | |
|---|---|
| PATENT NO. | : 11,071,593 B2 |
| APPLICATION NO. | : 15/650253 |
| DATED | : July 27, 2021 |
| INVENTOR(S) | : Kamyar Abhari et al. |

Page 1 of 1

It is certified that error appears in the above-identified patent and that said Letters Patent is hereby corrected as shown below:

In the Claims

In Column 24, Line 19 (Claim 8): "8. The system of claim 4, wherein the processor is further" should read -- 8. The system of claim 1, wherein the processor is further --.

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*